US010994291B2

(12) United States Patent
Wright

(10) Patent No.: US 10,994,291 B2
(45) Date of Patent: May 4, 2021

(54) ELECTROSTATIC FLUID DELIVERY SYSTEM

(71) Applicant: Victory Innovations Company, St. Louis Park, MN (US)

(72) Inventor: Clifford Wright, San Diego, CA (US)

(73) Assignee: Victory Innovations Company, Twinsburg, OH (US)

(*) Notice: Subject to any disclaimer, the term of this patent is extended or adjusted under 35 U.S.C. 154(b) by 0 days.

(21) Appl. No.: 17/090,820

(22) Filed: Nov. 5, 2020

(65) Prior Publication Data

US 2021/0053077 A1 Feb. 25, 2021

Related U.S. Application Data

(63) Continuation of application No. 16/803,801, filed on Feb. 27, 2020, which is a continuation of application (Continued)

(51) Int. Cl.
*B05B 5/025* (2006.01)
*B05B 5/03* (2006.01)
(Continued)

(52) U.S. Cl.
CPC .............. *B05B 5/0255* (2013.01); *A61L 2/14* (2013.01); *A61L 2/22* (2013.01); *A61M 11/00* (2013.01);
(Continued)

(58) Field of Classification Search
CPC ........ B05B 7/2408; B05B 7/241–2413; B05B 7/2464; B05B 5/03; B05B 5/0533; B05B 5/1691; B05B 15/65; B05B 15/656; B05B 7/0892; B05B 7/2416; B05B 7/2475; B05B 5/0255; B05B 5/10; B05B 9/0861;
(Continued)

(56) References Cited

U.S. PATENT DOCUMENTS 1,802,141 A * 4/1931 Downs .................... B05B 7/241
 239/367
2,591,585 A * 4/1952 Moore .................... E04F 21/12
 239/143

(Continued)

FOREIGN PATENT DOCUMENTS

CA 2 898 269 A1 7/2014
CN 1036343 A 10/1989
(Continued)

OTHER PUBLICATIONS

International Search Report Issued in PCT/US2015/048573 dated Dec. 10, 2015. 2 pages.

*Primary Examiner* — Cody J Lieuwen
(74) *Attorney, Agent, or Firm* — Mintz Levin Cohn Ferris Glovsky and Popeo, P.C.

(57) ABSTRACT

An electrostatic fluid delivery system is configured to deliver fluid, such as a disinfectant fluid, onto a surface by electrically charging the fluid and forming the fluid into a mist, fog, plume, or spray that can be directed onto a surface, such as a surface to be cleaned. The system atomizes the fluid using a high-pressure fluid stream and passes the fluid through an electrode of a nozzle assembly to charge droplets of the atomized fluid.

24 Claims, 23 Drawing Sheets

Related U.S. Application Data

Figure 1:
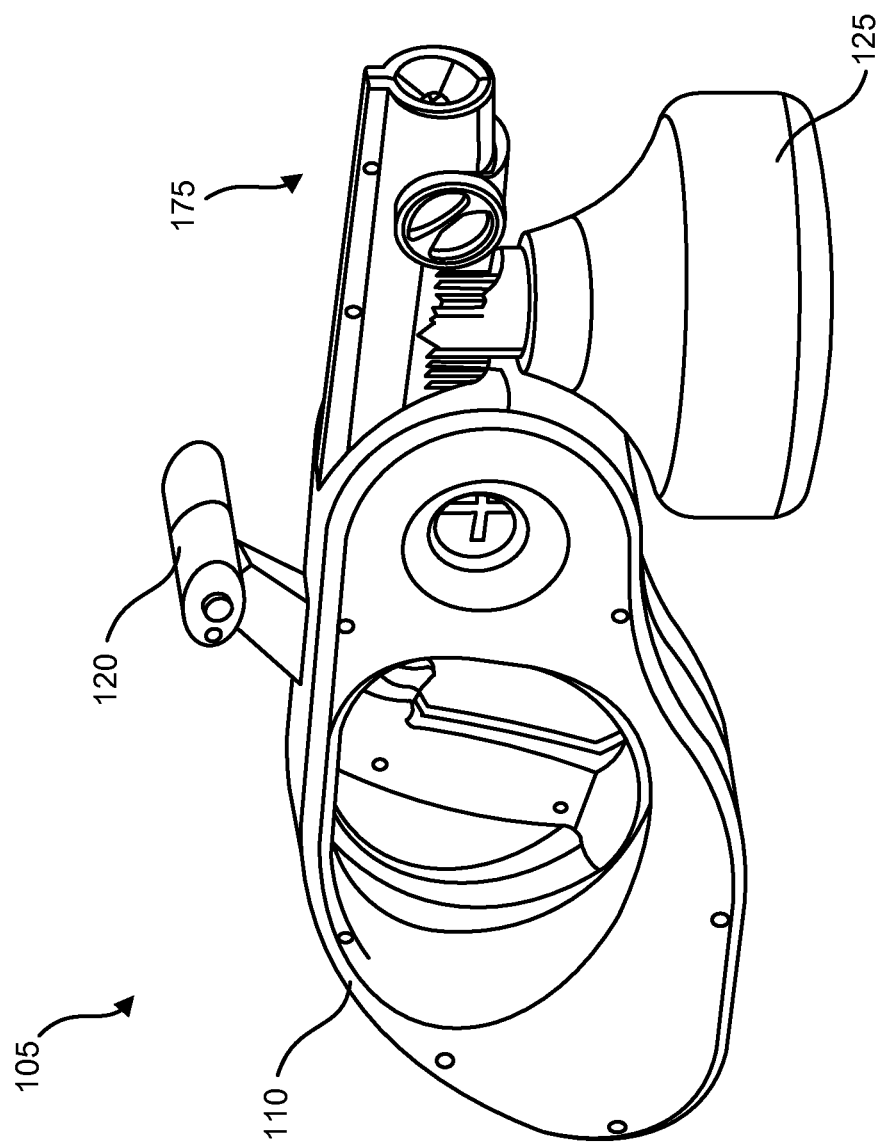
Figure 2:
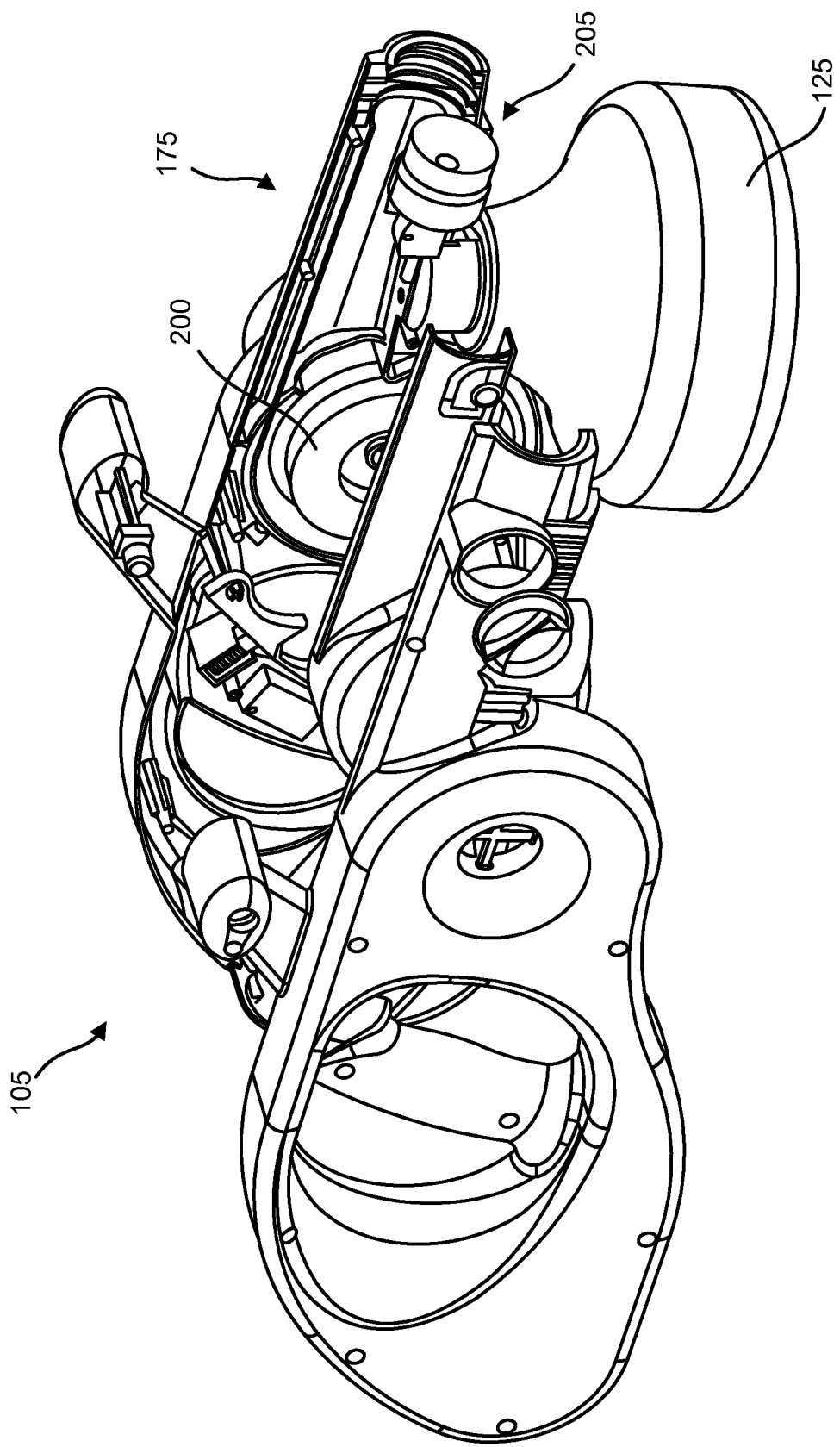
Figure 3:
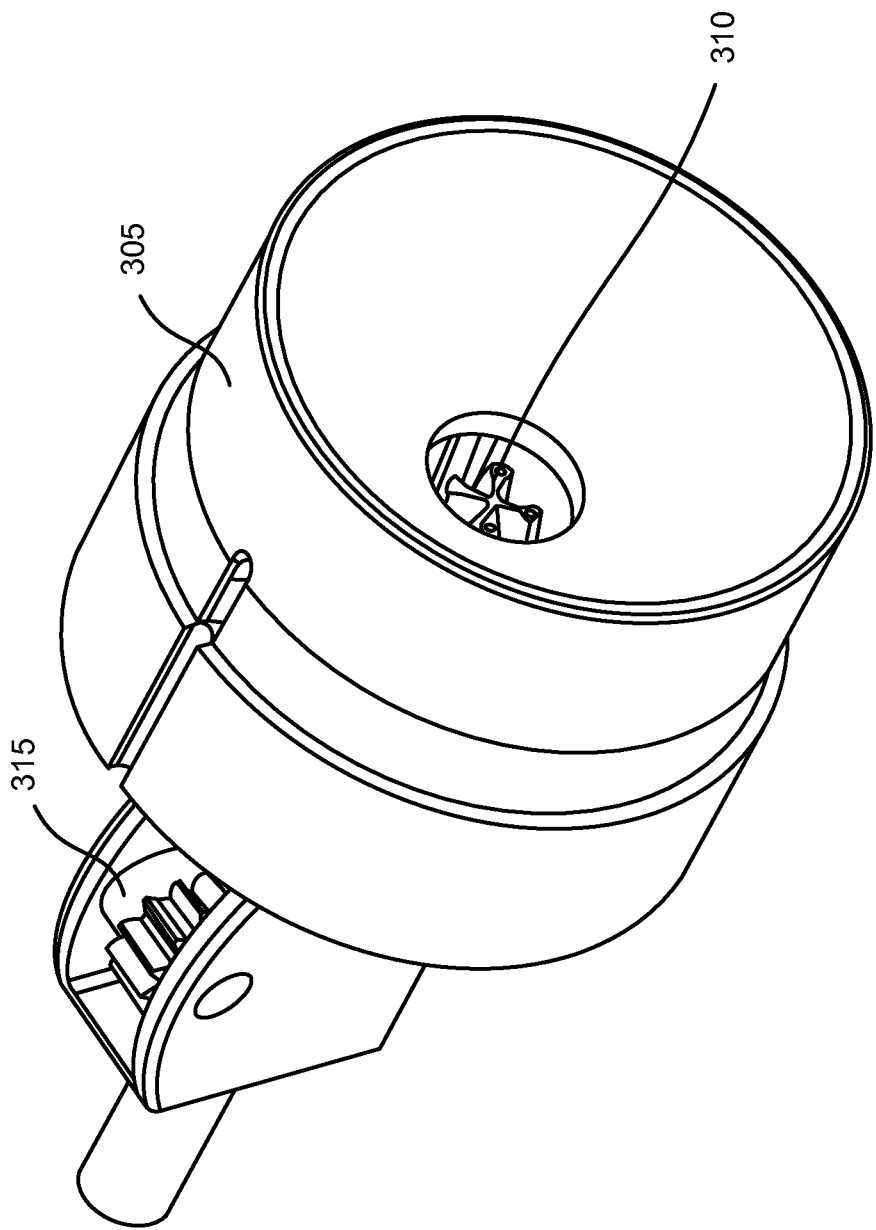
Figure 4:
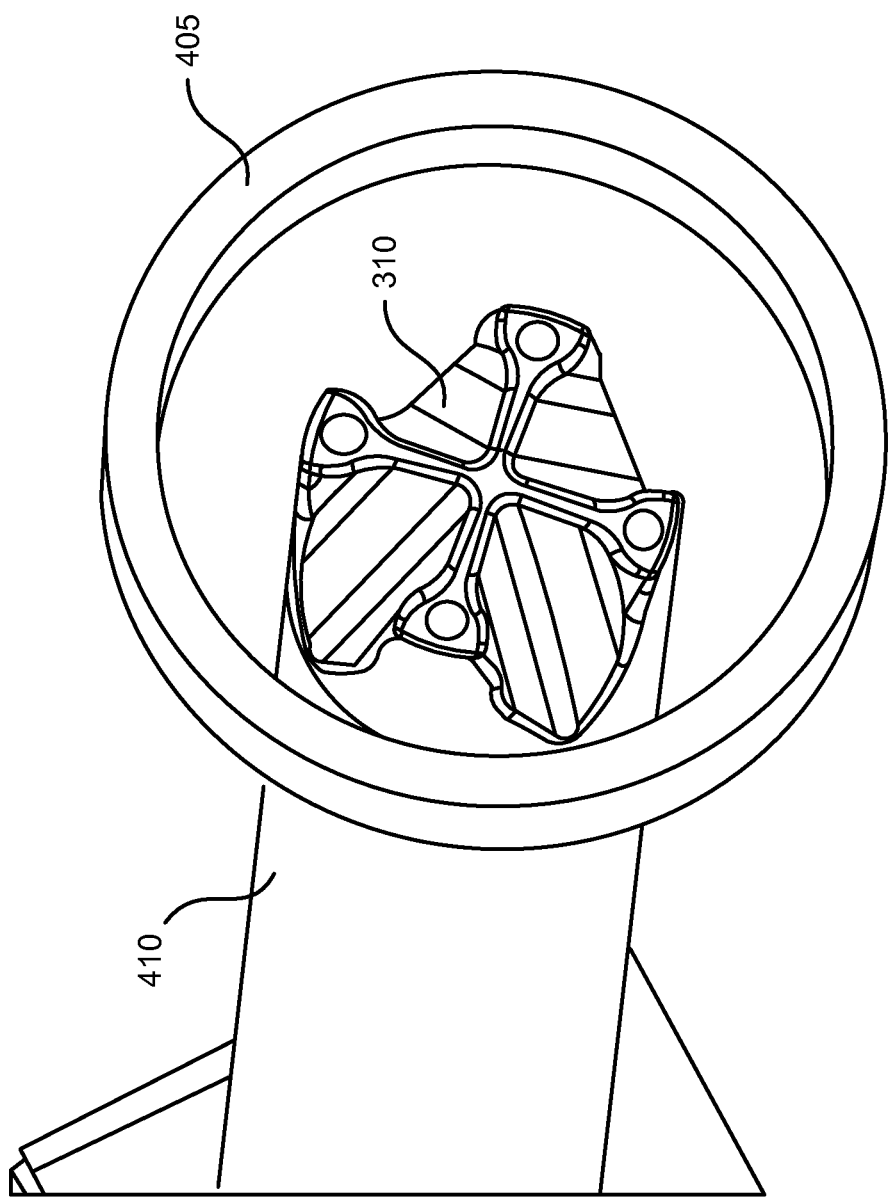

No. 15/507,456, filed as application No. PCT/US2015/048573 on Sep. 4, 2015, now Pat. No. 10,589,298.

(60) Provisional application No. 62/046,140, filed on Sep. 4, 2014.

(51) Int. Cl.
| | |
|---|---|
| *A61L 2/22* | (2006.01) |
| *B05B 9/08* | (2006.01) |
| *B05B 5/053* | (2006.01) |
| *B05B 5/16* | (2006.01) |
| *B05B 7/08* | (2006.01) |
| *B05B 7/24* | (2006.01) |
| *A61L 2/14* | (2006.01) |
| *B05B 15/656* | (2018.01) |
| *B05B 5/10* | (2006.01) |
| *A61M 11/00* | (2006.01) |

(52) U.S. Cl.
CPC .............. *B05B 5/03* (2013.01); *B05B 5/0533* (2013.01); *B05B 5/10* (2013.01); *B05B 5/1691* (2013.01); *B05B 7/0892* (2013.01); *B05B 7/2475* (2013.01); *B05B 9/0861* (2013.01); *B05B 15/656* (2018.02); *A61L 2202/15* (2013.01); *A61L 2202/25* (2013.01); *B05B 7/2416* (2013.01)

(58) Field of Classification Search
CPC .... A61L 2/22; A61L 2202/15; A61L 2202/25; A61L 2/14; A61M 11/00
USPC .......................................... 239/600, 706–708
See application file for complete search history.

(56) References Cited

U.S. PATENT DOCUMENTS

| | | |
|---|---|---|
| 3,166,239 A | 1/1965 | Greenhalgh |
| 3,630,441 A | 12/1971 | Felici et al. |
| 3,740,612 A | 6/1973 | Gauthier et al. |
| 4,358,059 A | 11/1982 | Coffee |
| 4,576,827 A | 3/1986 | Hastings et al. |
| 4,583,694 A | 4/1986 | Williams et al. |
| 4,848,660 A | 7/1989 | O'Connell |
| 5,121,884 A | 6/1992 | Noakes |
| 5,405,090 A | 4/1995 | Greene et al. |
| 5,501,400 A | 3/1996 | Kuo |
| 5,538,190 A | 7/1996 | Greene et al. |
| 5,779,162 A | 7/1998 | Noakes et al. |
| 5,932,011 A | 8/1999 | Noakes et al. |
| 5,984,199 A | 11/1999 | Restive |
| 6,216,966 B1 | 4/2001 | Prendergast et al. |
| 6,311,903 B1 | 11/2001 | Gaw et al. |
| 6,682,004 B2 | 1/2004 | Kadlubowski et al. |
| 6,708,908 B2 | 3/2004 | Heldt et al. |
| 6,866,212 B2 | 3/2005 | Sumiyoshi et al. |
| 7,007,826 B2 | 3/2006 | Shapanus et al. |
| 7,114,670 B2 | 10/2006 | Robidoux |
| 7,152,817 B2 | 12/2006 | Wilson et al. |
| 7,159,797 B1 | 1/2007 | Lammers |
| 7,182,280 B2 | 2/2007 | Ye et al. |
| D608,856 S | 1/2010 | Dammkoehler |
| D622,500 S | 8/2010 | Pho |
| 7,784,718 B2 | 8/2010 | Ohno |
| 7,823,808 B2 | 11/2010 | Yamaguchi et al. |
| 7,823,809 B2 | 11/2010 | Yamaguchi et al. |
| 7,841,549 B2 | 11/2010 | Yamaguchi et al. |
| 7,849,850 B2 | 12/2010 | Atterbury et al. |
| 7,883,032 B2 | 2/2011 | Davies et al. |
| 7,997,511 B2 | 8/2011 | Reynolds et al. |
| 8,074,640 B2 | 12/2011 | Davies et al. |
| D654,567 S | 2/2012 | Yamamoto et al. |
| 8,322,631 B2 | 12/2012 | Richardson et al. |
| 8,465,263 B2 | 6/2013 | Jones et al. |
| 8,496,194 B2 | 7/2013 | Baltz |
| 8,596,555 B2 | 12/2013 | Thompson et al. |
| 8,746,585 B2 | 6/2014 | Harwood et al. |
| 8,807,455 B2 | 8/2014 | Havlovitz et al. |
| 8,813,867 B2 | 8/2014 | Peterson et al. |
| 8,893,990 B2 | 11/2014 | Seitz et al. |
| D720,039 S | 12/2014 | Tinius |
| 9,016,599 B2 | 4/2015 | Johnson et al. |
| D731,027 S | 6/2015 | Sanz Perez |
| 9,085,008 B2 | 7/2015 | Kinne et al. |
| 9,149,109 B2 | 10/2015 | Slaton |
| 9,192,952 B2 | 11/2015 | Becker et al. |
| D749,192 S | 2/2016 | Fontaine |
| 9,259,748 B2 | 2/2016 | Pirrie |
| D757,214 S | 5/2016 | Richter et al. |
| D770,015 S | 10/2016 | Wright |
| 9,475,073 B2 | 10/2016 | Kinne et al. |
| 9,517,479 B2 | 12/2016 | Hines et al. |
| 9,604,234 B2 | 3/2017 | Thompson et al. |
| 9,604,235 B2 | 3/2017 | Thompson et al. |
| D818,701 S | 5/2018 | Wright |
| 2003/0006321 A1 | 1/2003 | Mather |
| 2003/0205631 A1* | 11/2003 | Barron .................... D06F 43/00 239/690 |
| 2005/0039738 A1 | 2/2005 | Zimlich et al. |
| 2005/0103893 A1* | 5/2005 | Birrenkott ............. B05B 7/0408 239/345 |
| 2005/0155972 A1* | 7/2005 | Ray .......................... B05B 1/12 220/694 |
| 2006/0081178 A1* | 4/2006 | Willey .................... B05B 5/025 118/621 |
| 2007/0048452 A1 | 3/2007 | Feng et al. |
| 2007/0194157 A1 | 8/2007 | Golden et al. |
| 2008/0105763 A1 | 5/2008 | Fahy et al. |
| 2008/0213499 A1 | 9/2008 | Matsumoto et al. |
| 2009/0026293 A1 | 1/2009 | Yamada et al. |
| 2010/0147700 A1 | 6/2010 | Field et al. |
| 2010/0237161 A1 | 9/2010 | Sandahl |
| 2012/0018478 A1 | 1/2012 | Hanna et al. |
| 2012/0223161 A1* | 9/2012 | Goodwin ............. A01C 23/047 239/375 |
| 2012/0234869 A1* | 9/2012 | Rigolio ................ B65D 21/086 222/325 |
| 2013/0240641 A1* | 9/2013 | Kinne ................... B05B 5/1691 239/289 |
| 2013/0330213 A1 | 12/2013 | Pilcher et al. |
| 2014/0110492 A1 | 4/2014 | Cooper |
| 2014/0110493 A1 | 4/2014 | Cooper |
| 2014/0158787 A1 | 6/2014 | Chen et al. |
| 2015/0314312 A1 | 11/2015 | Luczak et al. |
| 2015/0321215 A1 | 11/2015 | Huh et al. |
| 2017/0173607 A1 | 6/2017 | Wright |
| 2018/0085765 A1 | 3/2018 | Wright |

FOREIGN PATENT DOCUMENTS

| | | |
|---|---|---|
| CN | 1256973 A | 6/2000 |
| CN | 2605075 Y | 3/2004 |
| CN | 1962855 A | 5/2007 |
| CN | 201064744 Y | 5/2008 |
| CN | 103328107 A | 9/2013 |
| CN | 103611206 A | 3/2014 |
| EP | 0315615 A2 | 5/1989 |
| EP | 1 832 349 A1 | 9/2007 |
| JP | 2006-205158 A | 8/2006 |
| RU | 39839 U1 | 8/2004 |
| SU | 1826928 C | 7/1993 |
| WO | WO-2004/078244 A1 | 9/2004 |
| WO | WO-2014/055432 A1 | 4/2014 |
| WO | WO-2017/112781 A1 | 6/2017 |
| WO | WO-2018/195400 A1 | 10/2018 |

* cited by examiner

ELECTROSTATIC FLUID DELIVERY SYSTEM

CROSS-REFERENCE TO RELATED APPLICATIONS

This application is a continuation of U.S. patent application Ser. No. 16/803,801 filed on Feb. 27, 2020, which is a continuation of U.S. patent application Ser. No. 15/507,456 filed Feb. 28, 2017 and issued as U.S. Pat. No. 10,589,298 on Mar. 17, 2020. U.S. patent application Ser. No. 15/507,456 is a 371, of International Patent Application No. PCT/US2015/048573, filed on Sep. 4, 2015, which claims the benefit of and priority to U.S. Provisional Patent Application Ser. No. 62/046,140 entitled "ELECTROSTATIC FLUID DELIVERY SYSTEM DEVICE" and filed Sep. 4, 2014. The entire contents of each of the foregoing applications are hereby incorporated herein by reference in their entireties and for all purposes.

BACKGROUND

Infectious disease is too often acquired in places that should be safe, such as ambulances, hospitals, schools, restaurants, hotels, athletic facilities, and other public areas. These places are traditionally cleaned by spraying a fluid disinfectant onto surfaces and wiping down the surface with a cloth. Unfortunately such cleaning methods have been shown to be ineffective.

An improved mechanism for spraying down surfaces uses an electrostatic delivery system that sprays an electrically charged fluid, such as a disinfectant, onto surfaces. In an electrostatic delivery system, a fluid such as chemical solution is atomized by a high-pressure air stream as it passes through an electrode inside a nozzle. Negatively charged particles are thereby induced onto droplet surfaces of the solution to form electric field charge within the spray plume of the solution.

The electrostatic charge causes the fluid to cling to a surface to increase the likelihood that the disinfectant will cover and clean the surface. However, existing electrostatic delivery systems are unwieldy and inconvenient due to the power requirements of such systems. They are typically tethered to an electric cord or powered by air compressor or natural gas, which makes the system heavy. In addition, they are expensive. Cost and cording remain the two main obstacles to widespread adoption. In many cases existing corded products prohibit or restrict their use in applications where an extension cord is cumbersome, inconvenient, slow, and in some cases creating a safety concern by introducing a potentially dangerous tripping hazard.

In view of the foregoing, there is a need for improved electrostatic fluid delivery system.

SUMMARY

Figure 24:
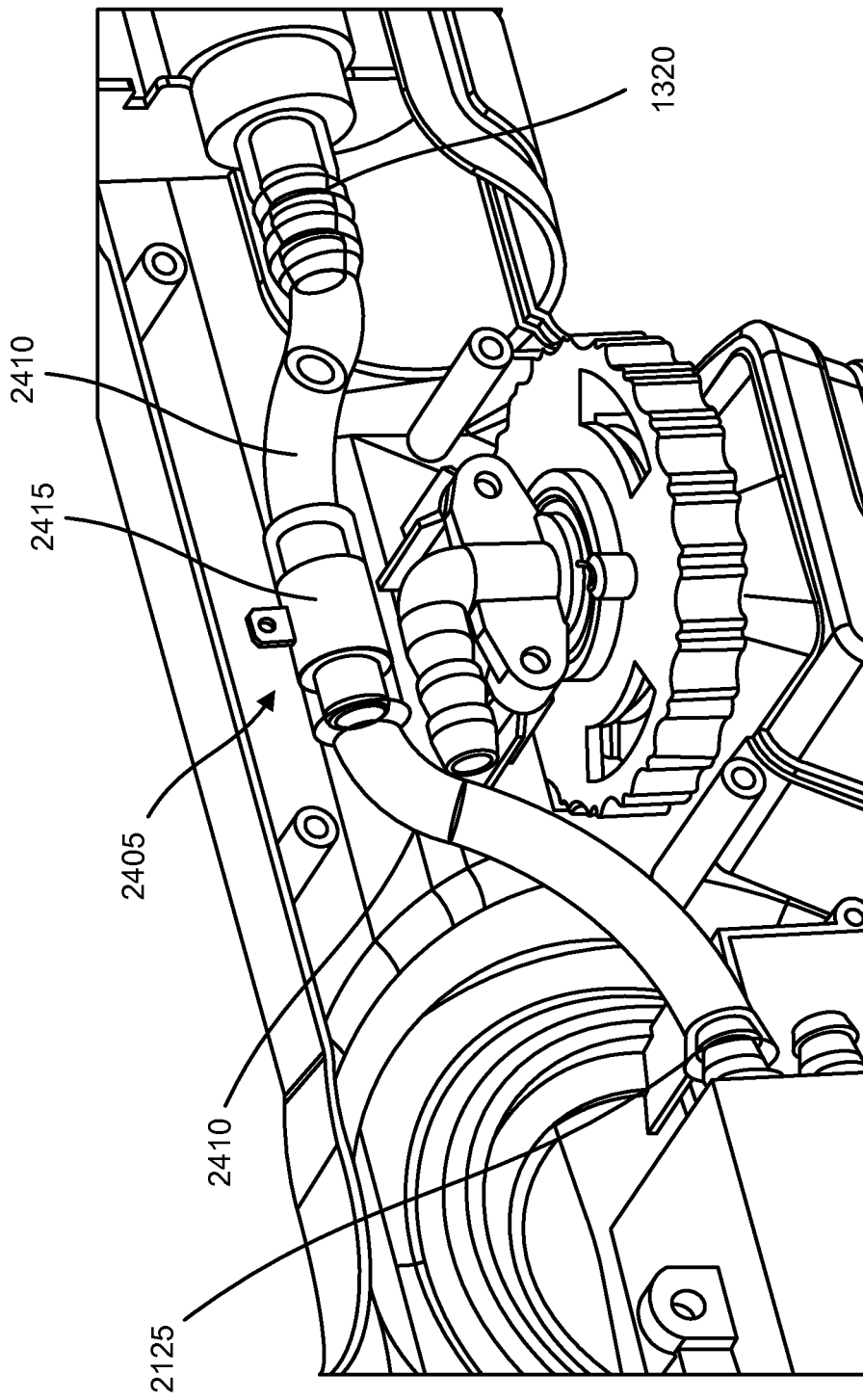

Disclosed herein is an electrostatic fluid delivery system that is configured to deliver fluid, such as a disinfectant fluid, onto a surface by electrically charging the fluid and forming the fluid into a mist, fog, plume, or spray that can be directed onto a surface, such as a surface to be cleaned. The system atomizes the fluid using a high-pressure air (or other gas) stream and passes the fluid through an electrode inside a nozzle assembly to charge, such as negatively charge, droplets of the atomized fluid. The system uses a unique nozzle design that is configured to optimally atomize the fluid into various sized droplets. In addition, the system is powered by a DC power system rather than an AC system to eliminate cumbersome power cords. In an embodiment, the DC power system includes a lithium ion battery. The device can electrically or positively charge a liquid or gas.

In one aspect, there is disclosed an electrostatic sprayer device, comprising: a housing; an electrostatic module inside the housing; a reservoir having a cavity adapted to contain a fluid; at least one nozzle fluidly connected to the reservoir wherein the nozzles emit fluid in a direction along a flow pathway; a pump that propels fluid from the reservoir to the at least one nozzle; a direct current battery that powers at least one of the electrostatic module and the pump; an electrode assembly that electrostatically charges the fluid, wherein the electrode assembly is at least one of: (1) a first electrode assembly formed of a plurality electrodes electrically attached to the electrostatic module, wherein each electrode emits ions along an axis that is parallel to the flow pathway of the fluid emitted from the nozzle such that the plurality electrodes form a static electrical field through which the fluid passes; and (2) a second electrode assembly formed of a tube that fluidly through which fluid flows from the reservoir toward the at least one nozzle, wherein at least a conductive portion of the tube is electrically attached to the electrostatic module, and wherein the conductive portion of the tube physically contacts the fluid as it flows through the tube and applies an electrical charge to the fluid.

Other features and advantages should be apparent from the following description of various embodiments, which illustrate, by way of example, the principles of the disclosure.

BRIEF DESCRIPTION OF THE DRAWINGS

FIG. 1 shows a perspective view of an electrostatic fogger device.

FIG. 2 shows an exploded view of the device of FIG. 1.

FIG. 3 shows an enlarged view of a nozzle assembly of the device.

FIG. 4 shows a close up view of a nozzle surrounded by a charging ring.

FIGS. 5 and 6 show a backpack style fogger.

FIG. 7 shows an embodiment of a handheld fogger.

FIG. 8 shows another embodiment of a handheld fogger.

FIG. 9 shows another embodiment of an electrostatic fogger device.

FIG. 10 shows the device of FIG. 9 with a portion of an outer housing removed.

FIG. 11 shows a nozzle assembly of the device.

FIG. 12 shows a nozzle assembly of the device with a nozzle tool attached thereto.

FIG. 13 shows a nozzle housing of the nozzle assembly.

FIG. 14 shows a nozzle component with nozzles.

FIG. 15 shows an electrode assembly.

FIG. 16 shows an electrode.

FIG. 17 shows a perspective view of the nozzle tool.

FIG. 18 shows an enlarged view of a handle region of the system.

FIG. 19 shows an enlarged view of a handle region of the system with a portion of the outer housing removed.

FIG. 20 shows an interior of a cap of a liquid or fluid reservoir of the system.

FIG. 21 shows a perspective view of the reservoir.

FIG. 22 shows a perspective view of the system with the reservoir removed.

FIG. 23 shows an exemplary embodiment of the pump of the system.

FIG. 24 shows an ion tube isolator that provides a positive or negative electrical charge to fluid flowing the tube isolator via direct contact with the fluid,

DETAILED DESCRIPTION

Before the present subject matter is further described, it is to be understood that this subject matter described herein is not limited to particular embodiments described, as such may of course vary. It is also to be understood that the terminology used herein is for the purpose of describing a particular embodiment or embodiments only, and is not intended to be limiting. Unless defined otherwise, all technical terms used herein have the same meaning as commonly understood by one skilled in the art to which this subject matter belongs.

Figure 6:
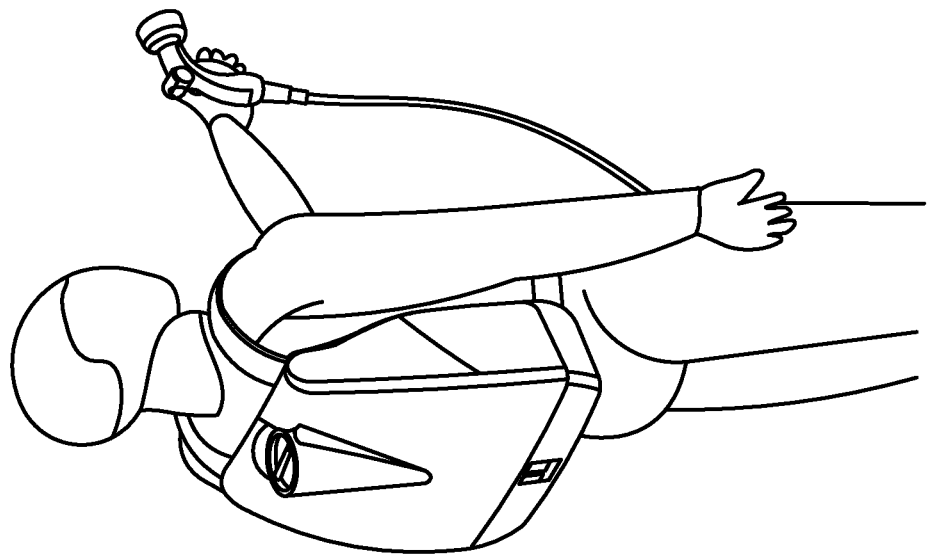
Figure 5:
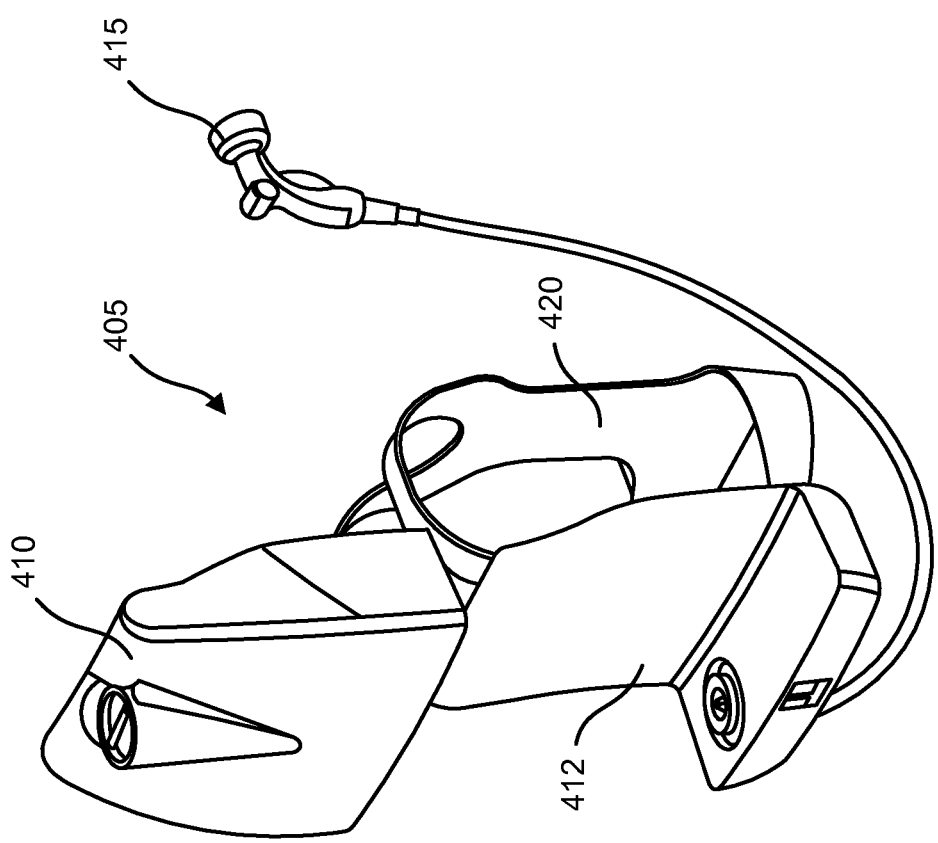

Disclosed herein is an electrostatic fluid delivery system that is configured to deliver fluid, such as a disinfectant fluid, onto a surface by electrically charging the fluid and forming the fluid into a mist, fog, plume, or spray that can be directed onto a surface, such as a surface to be cleaned. The system atomizes the fluid using a high-pressure air (or other gas) stream and passes the fluid through an electrode inside a nozzle assembly to charge, such as negatively charge, droplets of the atomized fluid. The system uses a unique nozzle design that is configured to optimally atomize the fluid into various sized droplets. In addition, the system is powered by a DC power system rather than an AC system to eliminate cumbersome power cords. In an embodiment, the DC power system includes a lithium ion battery. The device can electrically or positively charge a liquid or gas.

The system is configured to electrostatically charge the atomized fluid via direct charging, induction charging, indirect charging, or any combinations thereof. In the case of direct charging, fluid flows through an electrically conductive tube or other conduit that is electrostatically charged such that the fluid contacts the tube and is charged by direct contact with the tube, as describe below. For induction or indirect charging, the fluid is passed through a medium, such as air, that has been electrostatically charged by one or more electrodes or pins that create a static electric field through which the fluid passes to receive c charge. The electrode may or may not be in the fluid stream. In an embodiment, the fluid is charged through both direct contact with the charged tube and by flowing the fluid through a medium such as air that has been charged with electrodes such as, for example, described herein.

FIG. 1 shows a perspective view of an electrostatic fluid delivery system 105 that is configured to electrically charge and atomize a fluid for spraying onto a surface. The system 105 includes a housing 110 that is sized and shaped to be held by a user. The housing 110 has an ergonomic shape that can be easily grasped and held but it should be appreciated that the size and shape of the housing can vary. In an embodiment, one or more vents or openings are positioned in the outer housing to provide communication between an inside of the outer housing and the outside such as for venting.

The system 105 may have one or more actuators or controls 120 that can be actuated by a user to activate and operate the system. A fluid expelling region 175 is located at a front of the housing 110 and has an opening through which atomized fluid is expelled. The system 105 also includes a reservoir 125 that defines a chamber in which fluid can be stored. The chamber of the reservoir 125 communicates internally with a nozzle assembly 205 (FIG. 2) for supplying fluid to be electrically charged and atomized by the nozzle assembly, as described more fully below.

FIG. 2 shows the system 105 in an exploded state. The housing is formed of multiple pieces that connect to contain an inner region in which is housed a fan 200. The fan 200 is powered by a battery, such as a lithium ion battery. An electrical circuit board converts the DC power to AC power for powering the fan. The system may include a stator coupled to the battery as well as a protection circuit module (PCM).

The fan 200 (or a pump) operates to blow fluid (gas or liquid) toward a nozzle assembly 205 in the fluid expelling region 175 of the system. The nozzle assembly 205 atomizes and expels fluid in a spray. As the fan blows air toward the nozzle assembly, it creates a pressure differential that sucks fluid from the reservoir 125 into the nozzle assembly 205 where it is atomized and expelled as a result of the fan 200 blowing air therethrough. It should be appreciated that other mechanisms can be used to blow air or to blow or otherwise propel liquid from the reservoir. In an embodiment, a piston pump is used to deliver air pressure to the nozzle tip. A piston pump can pull from the reservoir tank to push fluid or pressurize straight to the nozzle tip. For a smaller footprint embodiment (such as the embodiments of FIGS. 7 and 8) a Pneumatics Micro Pump can act as a solenoid pulling fluid by a magnetic movement. The device can also include a pump that pulls a vacuum in the reservoir or fluid tank to cause fluid to flow out of the reservoir toward the nozzles(s).

FIG. 3 shows an enlarged view of the nozzle assembly, which includes an annular housing 305 having a central opening in which is positioned a nozzle 310. The housing 305 has a conically or frustoconically shaped surface that can be curved or straight. The surface is shaped such that fluid from the nozzle 310 bounces back and forth along the surface to form a turbulent flow that atomizes the fluid. In an embodiment, the fluid is atomized to droplets in the range of 5 microns to 40 microns in size. The nozzle 310 is mechanically coupled to a drive assembly 315 that moves the nozzle 310 relative to the housing to control the size of the droplets. In this manner, the user can move the nozzle back and forth to achieve a desired plume profile.

FIG. 4 shows an enlarged view of the nozzle 310. The tip of the nozzle 310 is positioned centrally within a charge ring 405 that is positioned within the housing 305 (FIG. 3) in the assembled device. The charge ring 405 is positioned as such (deep inside the housing) to reduce the likelihood of a user touching the charged ring. The charge ring 405 is grounded and also electrically connected to a power source for achieving a positive voltage on the charge ring 405 during use. As the nozzle 310 expels the atomized fluid through the charge ring 405, it positively charges the fluid. In this manner, the electrically charged plume of fluid will cling to surfaces that it is sprayed upon.

With reference still to FIG. 4, the nozzle 310 has a series of openings through which fluid is expelled. The openings communicate with an internal lumen of a tube 410 through which fluid flows from the reservoir 125 (FIG. 1). The openings are arranged in a unique spatial pattern comprised of four openings with each opening positioned 90 degrees away from an adjacent opening so as to form a cross pattern. The openings can vary in size. In an embodiment, the openings are 0.063 inches in diameter. As mentioned, the nozzle can be connected to a drive assembly that varies the position of the nozzle to control the plume profile.

The electrostatic fluid delivery system may vary in size and shape. FIGS. 5 and 6 show a backpack embodiment 405 that is configured to be worn on the back of user. The system includes a fluid tank 410 that is removably mounted to a frame 412 such that the tank 410 can be interchanged with another tank. The frame 412 is connected to a harness 420 or other support for mounting on a user's back, as shown in FIG. 6. The tank 410 is fluidly connected to a handheld nozzle 415 through which a plume of electrically charged fluid is expelled. The backpack embodiment can include any component of the other systems described herein, including the electrostatic configurations and removable reservoir.

Figure 7:
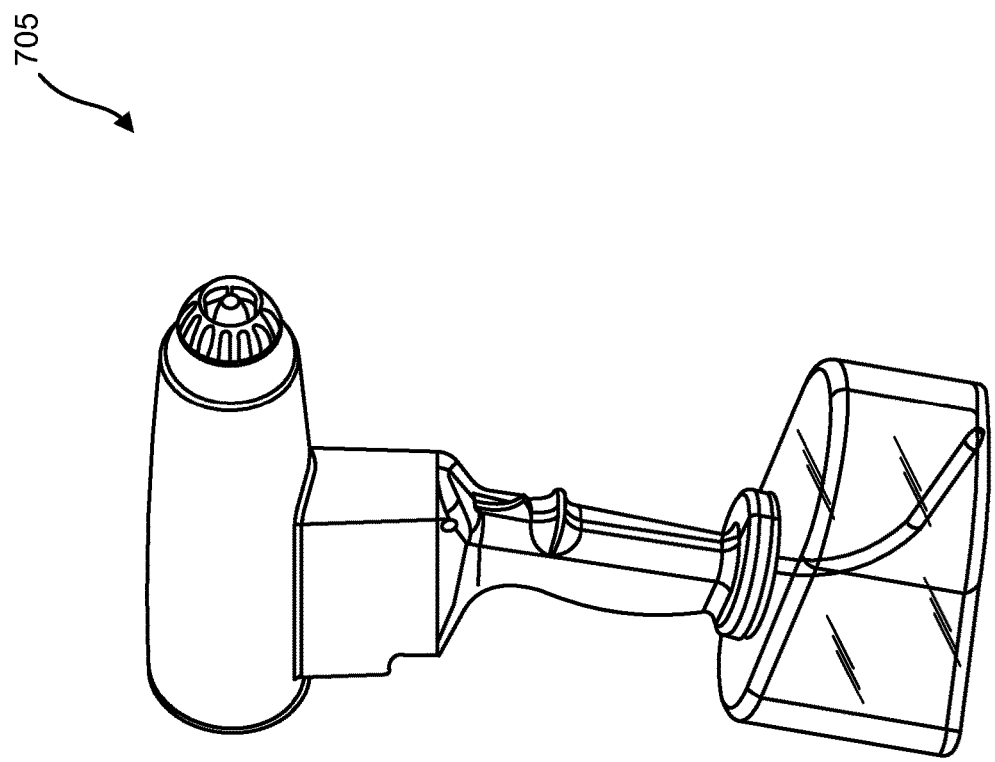
Figure 8:
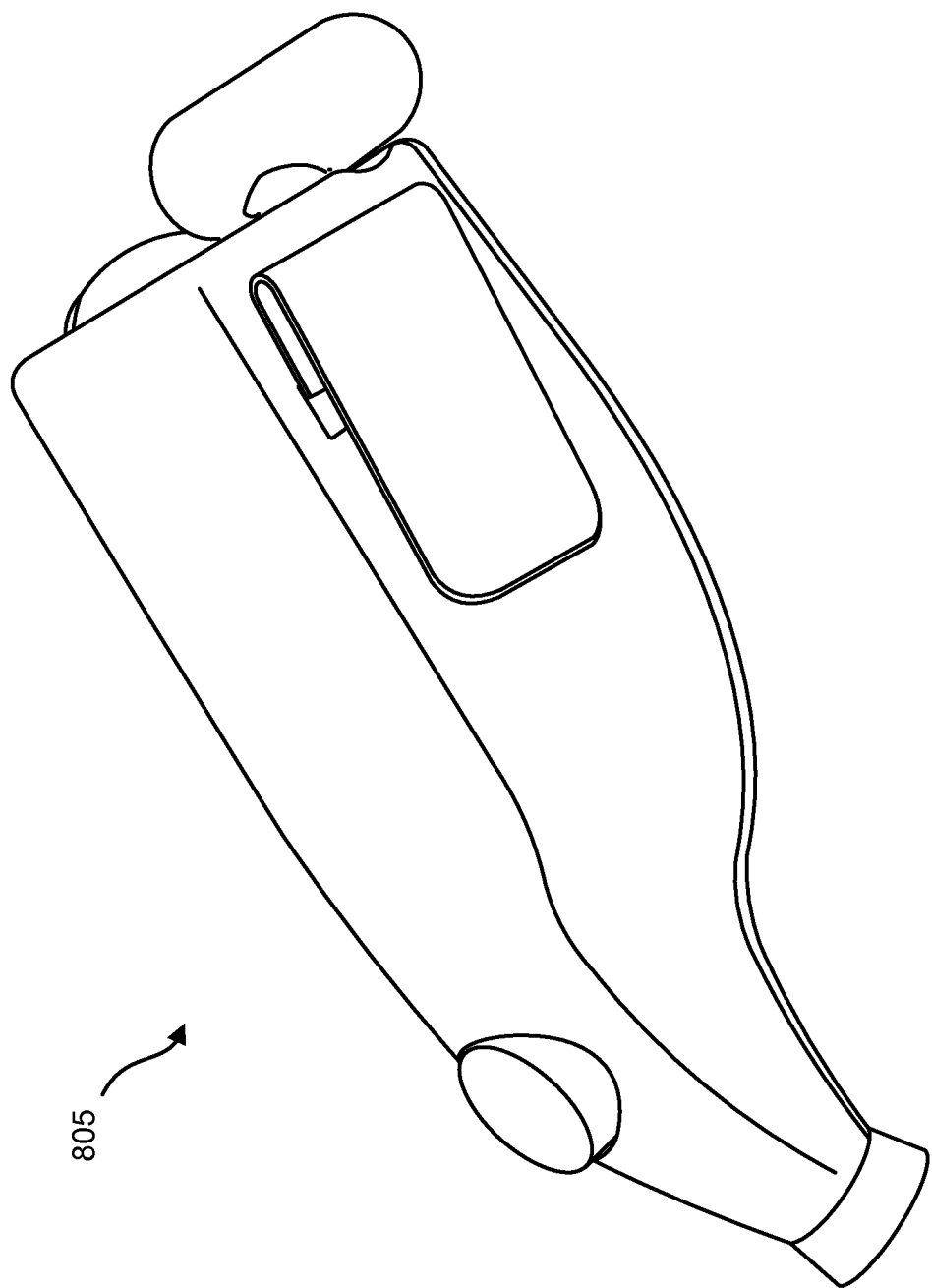

In addition, FIG. 7 shows another handheld embodiment 705 having a reservoir at a bottom of the device. FIG. 8 shows an embodiment 805 that has a hand pump that can be pumped to generate a pressure differential that expels a plume of fluid out of the device.

Figure 9:
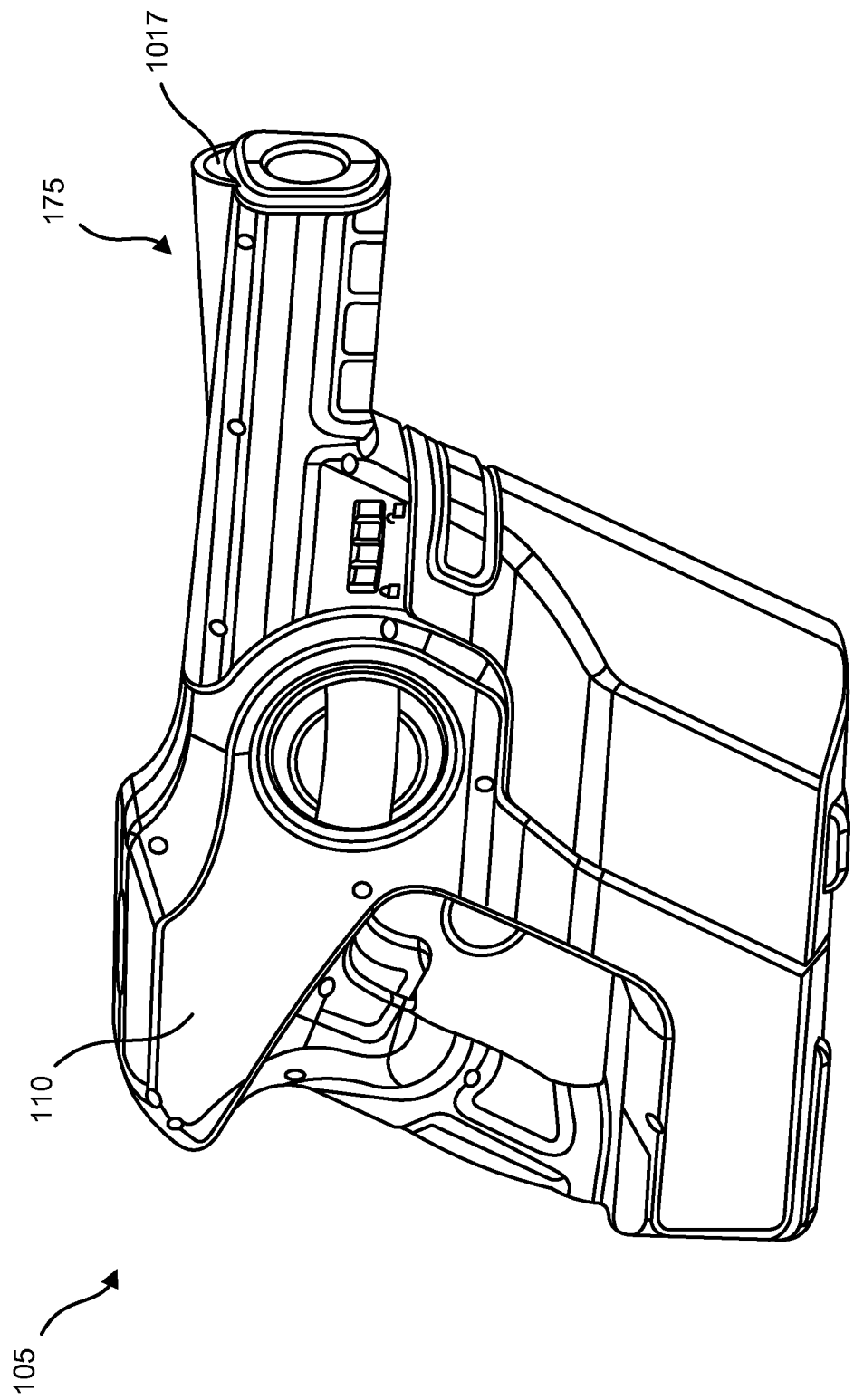

FIG. 9 shows another embodiment of the system 105. As in the previous embodiment, the system 105 has an outer housing 110 that forms a handle that can ergonomically be grasped by a single hand of a user. The system 105 includes at least one actuator that can be actuated to turn on and also turn off an internal pump, as well as a second actuator for turning on and off an electrostatics charger for expelling a plume of electrostatically charged fluid from a fluid expelling region 175 of the system 105. The system 105 has a removable reservoir 125 for storing fluid to be expelled.

The system 105 ejects high voltage ions to the air by means of a plurality of (such as three or more) sharp, detachable high voltage ion discharge electrodes or pins of a predetermined spacing (such as at 120° spacing) from each other on a rim of a nozzle holder (described below with reference to FIG. 14). The high voltage ion discharge electrodes are each positioned along an axis that is in parallel to an axis of a spray nozzle so that the spray and ions are emitted in the same direction and along a parallel axis and therefore the droplets in the spray are surrounded and covered by ion stream and can be efficiently charged when they meet the ion stream. The electrodes thus emit, propel, or otherwise send out ions or charge in a direction parallel to the direct of fluid flow or an average direction of fluid flow from the nozzles.

Figure 10:
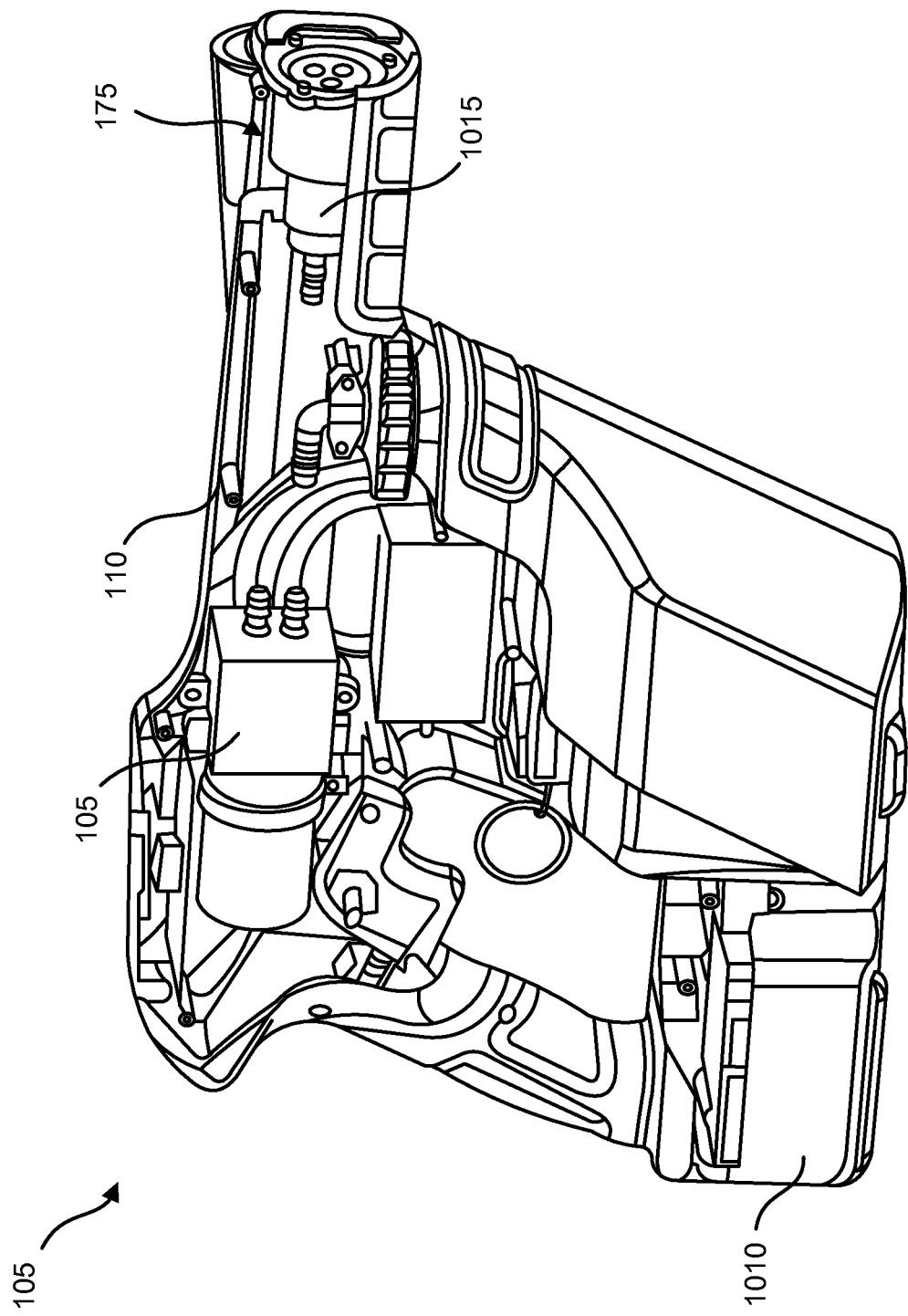

FIG. 10 shows the system 105 with a portion of the outer housing 110 removed to show internal components of the system 105. The system 105 includes a pump 1005 that is powered by a battery 1010. The pump 1005 is fluidly coupled to fluid within the reservoir 125 such that the pump can cause a pressure differential to draw fluid from the reservoir and into a nozzle assembly 1015, which is described in detail below. The system 105 further includes an electrostatic module that is electrically connected to an electrostatic ring, as described below. The electrostatic module in an example embodiment is a 12 kV electrostatic module and it is configured to electrostatically charge an item, such as the electrodes, ring, and/or tube described below.

In an embodiment, a light 1017 is positioned at a front end of the system 105 in the fluid-expelling region 175 such that the light aims light toward the direction where fluid is expelled. The light may be an LED light, for example. The light can automatically illuminate when any portion of the system is activated. In an example embodiment, LED light has 100 lumens with the light being directly focused on the path of the liquid that is being sprayed out of the sprayer nozzle. The light can be in multiple colors to allow the user to illuminate florescent antimicrobial solutions (infrared light). In another embodiment the light is black light. At least a portion of the light or electrical components of the light may be insulated from contact with the electrically charged field.

Figure 11:
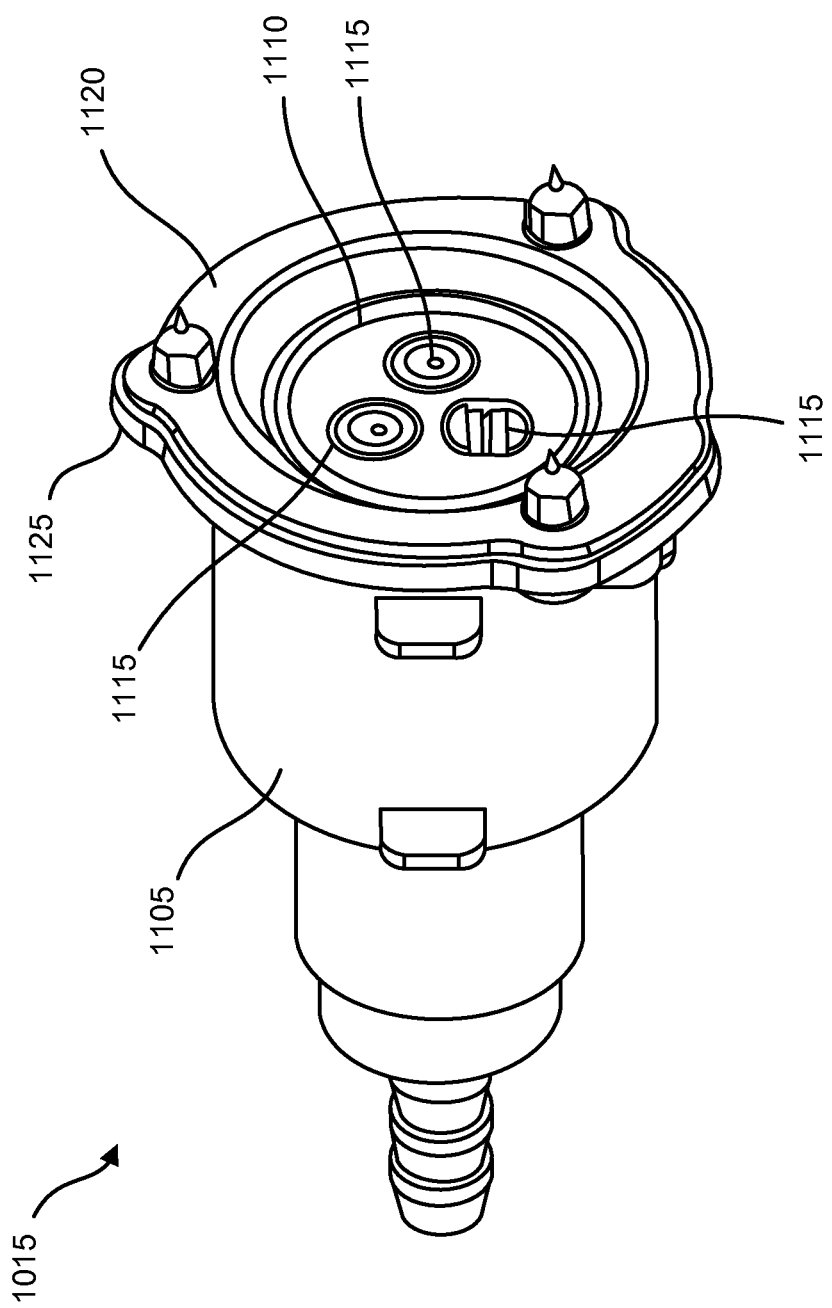
Figure 12:
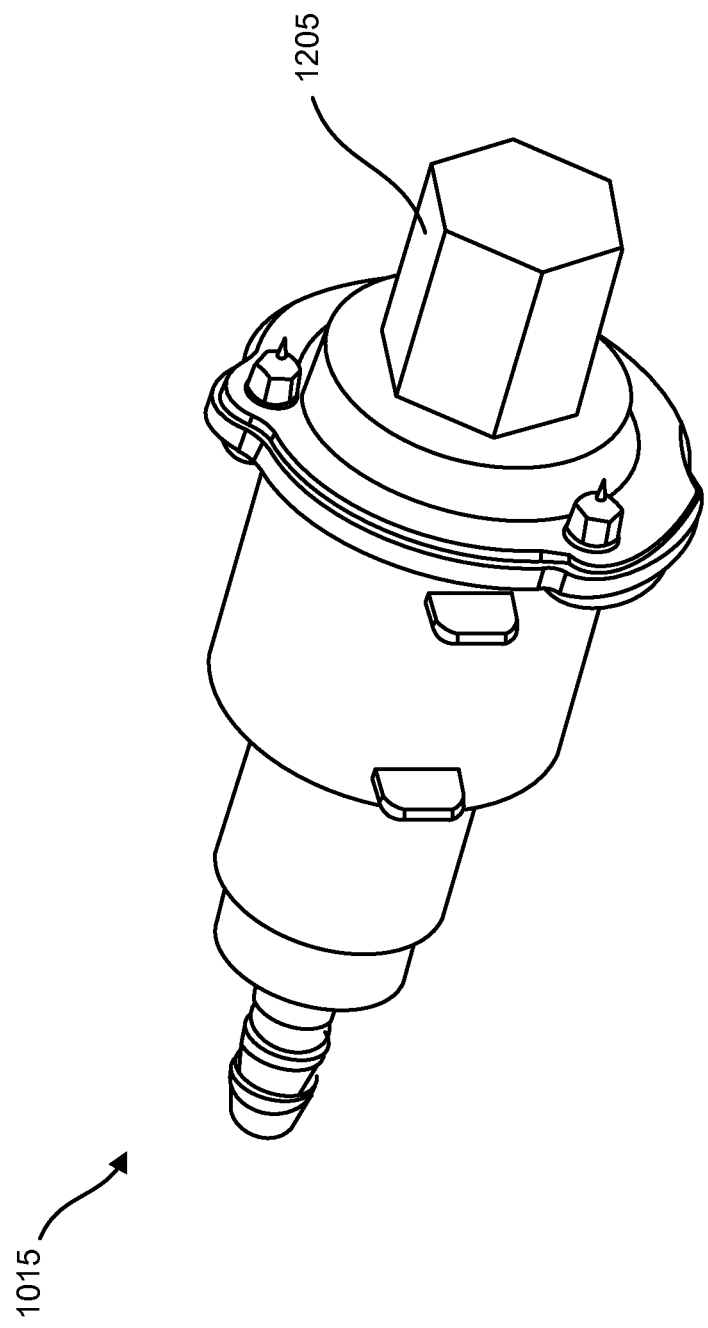

FIG. 11 shows a perspective view of the nozzle assembly 1015, which includes a nozzle housing 1105 having an internal cavity that removably contains a nozzle holder or nozzle component 1110 in which one or more nozzles 1115 are positioned. An annular electrostatic ring 1120 is mounted on a forward edge of the nozzle housing 1105. The electrostatic ring 1120 forms an opening through which fluid is expelled from the reservoir and through at least one of the nozzles by virtue of the pump creating a pressure differential. An insulator element, such as a rubber ring 1125 is positioned on the electrostatic ring 1120 to electrically shield it from the outer housing 110 of the system.

There is a metal contact on the high voltage electrostatic ring 1120 that is exposed at a rear part of the electrostatic ring 1120. A high voltage wire from the electrostatic module is soldered or otherwise electrically connected to this metal contact. The soldering point and adjacent exposed metal is completely sealed by epoxy or other insulator to avoid oxidation and leakage of ions from the electrodes. A ground wire from electrostatic module is connected to ground plate. As discussed, the ground wire is embedded in the handle of the sprayer so that it is in contact with the operator during operation. This serves as electrical return loop to complete an electrical circuit. The electrostatic ring is electrically charged so that it transfers the charge to the electrodes that are electrically connected to the ring. In another embodiment, the electrodes themselves are individually connected to the electrostatic module.

As shown in FIG. 12, the system 105 also includes a nozzle tool 1205 that removably and mechanically couples to the nozzle assembly for manipulating the nozzle component 1110. The nozzle tool 1205 is sized and shaped to be inserted into a front opening in the nozzle housing 1105. When inserted into the nozzle housing 1105, the nozzle tool 1205 mechanically couples to the nozzle component 1110 in a manner that permits the nozzle tool 1205 to lock and/or move the nozzle component 1110 relative to the nozzle housing 1105, as described more fully below.

In an embodiment, the tool 1205 couples to and removes nozzle component by a counter clock turn and by pushing in until nozzle component decouples and can be removed. In this regard, pushing the nozzle component deeper into the housing using the tool causes a threaded portion of the nozzle component to engage a threaded nut or bolt of the housing that secures the nozzle component to the housing. The user can then unthread the nozzle tool and remove it from the housing.

The tool 1205 can also be used to adjust the three-way nozzle by turning it in a desired rotational direction. The user can select three different spray patterns by turning the nozzle component so that a desired nozzle fluidly couples to the reservoir. In this regard, a portion of the tool mechanically attaches to the nozzle component so that it can apply force to the nozzle component and rotate it until a desired nozzle is in a position that is fluidly coupled to a fluid stream from the reservoir. The system may include a mechanism, such as spring and ball, that provides a noise (such as a clicking sound) when a nozzle is in a position to spray fluid.

FIG. 17 shows a perspective view of the nozzle tool 1205. The nozzle tool 1205 is sized and shaped to be grasped by a user. It includes a coupler region 1705 that can be removably coupled to a drive device, such as a wrench, or grasped by a user. In an embodiment, the coupler region 1705 is hexagonal shaped so that it can be mechanically coupled to a wrench including a socket wrench. The nozzle tool 1205 includes a cavity or seat 1710 that is size and shaped to receive the outer portion of the nozzle component.

For example, the seat 1710 can have a shape that complements and receives the shape of the nozzle component 1110. The nozzle tool 1205 also includes at least one opening 1715 that interlocks with a complementary-shaped protrusion 1405 (FIG. 14) on the nozzle component 1110.

Figure 13:
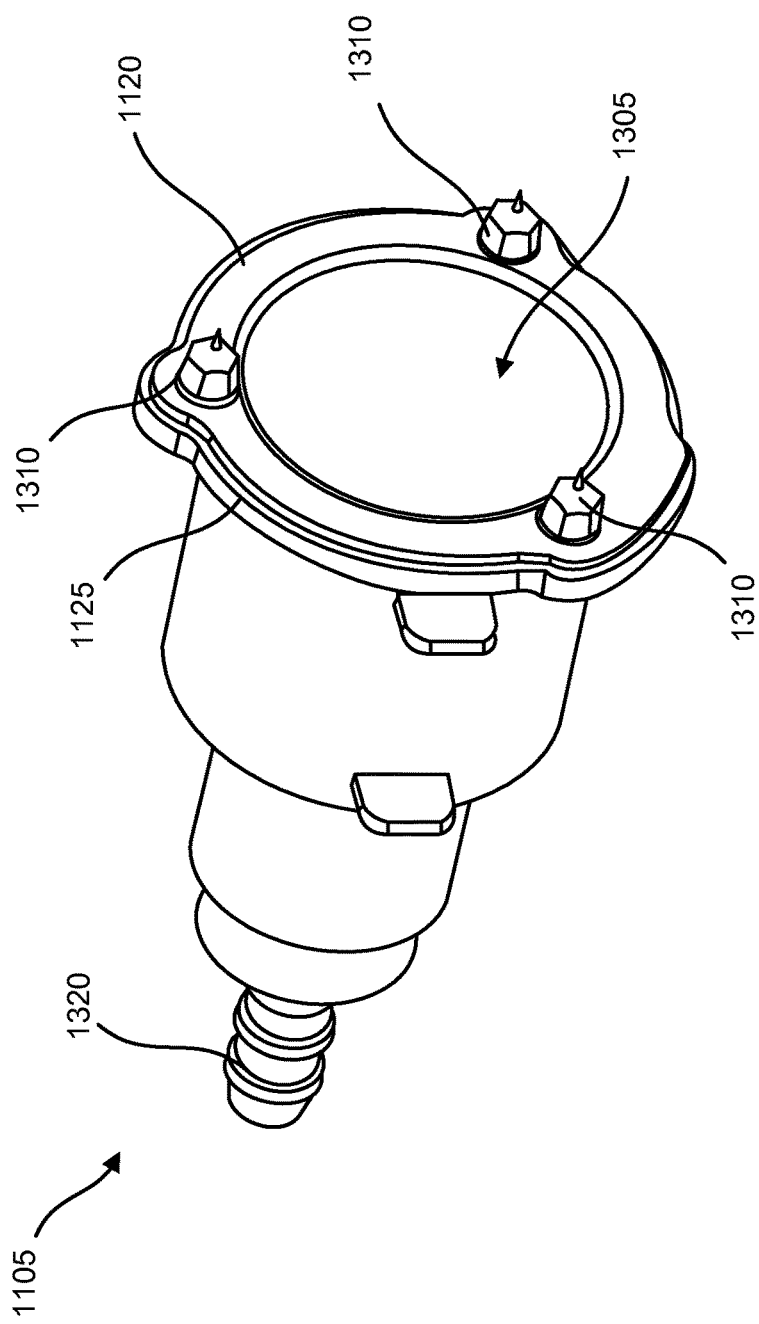

FIG. 13 shows a perspective view of the nozzle housing 1105 without the nozzle component 1110 mounted therein. The nozzle housing 1105 has an elongated, cylindrical shape and defines an internal cavity 1305 sized to removably receive the nozzle component 1110. The electrostatic ring 1120 is mounted at the front edge of the nozzle housing 1105 with the rubber ring 1125 positioned in a seat within the electrostatic ring 1120. The rubber ring 1125 insulates a set of three electrode assemblies 1310 that are mounted on the electrostatic ring 1120 in a predetermined position and orientation. The electrodes assemblies 1310 are arranged around the opening of the nozzle housing 1105 around the nozzles of the nozzle component 1110 when it is positioned in the nozzle housing 1105. In an embodiment, the electrode assemblies 1310 are positioned at 120 degree increments around the electrostatic ring 1120.

The electrostatic ring 1120 includes the three electrodes (which may be made or stainless steel for example) that are electrically isolated by a rubber washer and rubber threaded cap, as described below. The electrostatic ring 1120 that holds electrodes is metal and is built inside of the nozzle housing. The electric static ring is isolated inside a nozzle housing that acts as a protective barrier. The electrostatic ring 1120 contains three internal threaded holes that accept the three electrodes. A rubber washer is inserted between the electrostatic ring 1120 and an insulator on each electrode. The rubber washer aids in tightening of the electrode to the electrostatic ring 1120 and also assists in avoiding leakage of ions from the electrode. The whole electrostatic ring 1120 is isolated inside the nozzle housing so that it acts a protective barrier.

The ring, when properly mounted, forms a safety gap between the discharge electrodes and the outer housing so as to minimize static leakage through the housing. The rubber ring isolates the nozzle housing from causing a charge to the sprayer housing. The rubber ring also isolates the nozzle housing from main body of the sprayer to prevent water from penetrating to a main body of the sprayer.

A hose coupler 1320 is located at an end of the nozzle housing and is configured to be coupled to a house or other conduit that communicates with the reservoir. The hose coupler 132 defines an internal passageway that communicates with the nozzles 1115 for feeding fluid from the reservoir to the nozzles 1115.

Figure 14:
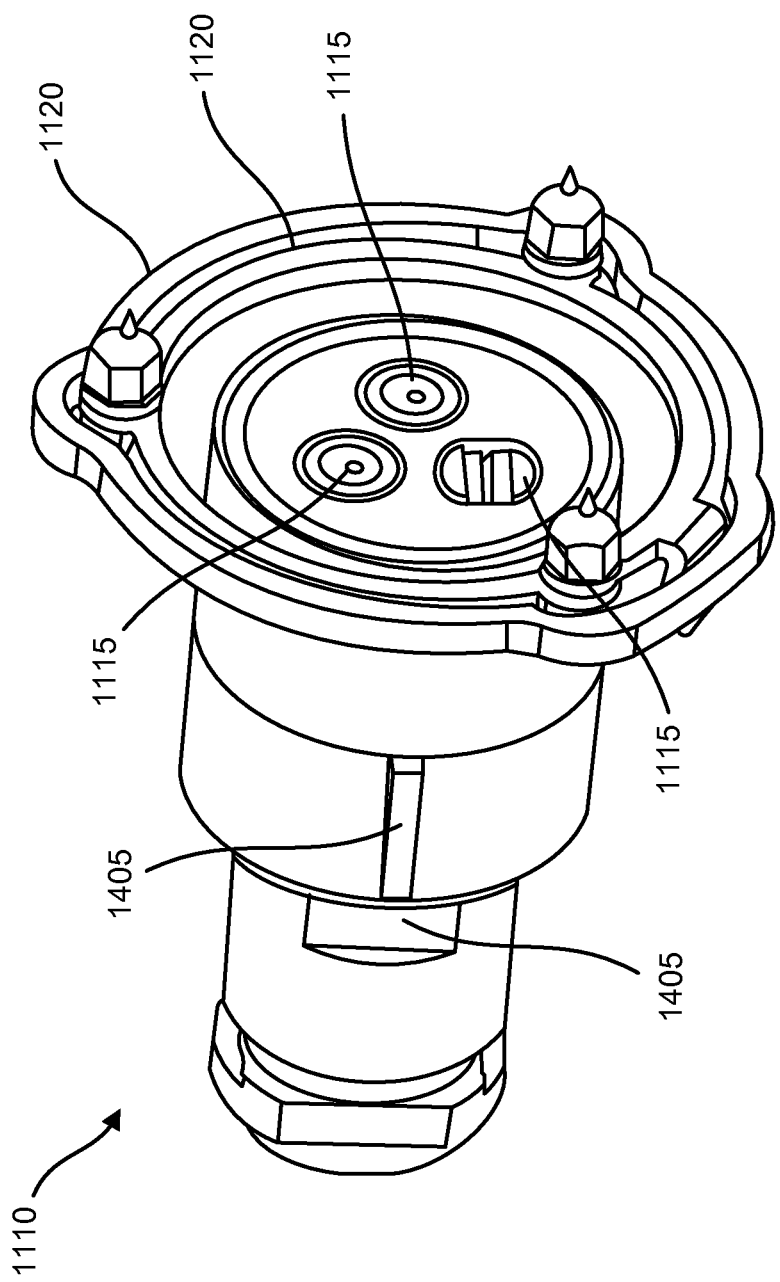

FIG. 14 shows the nozzle component 1110, which is sized and shaped to be removably positioned within the cavity 1305 of the nozzle housing 1105. The nozzle component 1110 houses one or more nozzles 1115, each of which is configured to deliver fluid in a predetermined plume or spray pattern. The nozzle component 1110 includes one or more protrusions 1405 or other structural elements that are sized and shaped to receive complementary structures on the nozzle tool 1205, as described below. Note that the electrostatic ring 1120 with the electrode assemblies 1310 is positioned around the nozzles 1115 with the electrodes of the assemblies 1310 being aligned along an axis that is parallel with an axis of the nozzles.

Any of a variety of nozzle types can be used to achieve a desired flow pattern. There are now described some non-limiting examples of electrodes. In an embodiment, the electrodes include three example types as follows:

(1) A nozzle that provides a cone-shaped spray, with a flow rate of 0.23 L/min, 45° @3.5 bar, SMD=113 um, inner orifice=0.65 mm;

(2) A nozzle that provides a cone-shaped spray, with a flow rate of 0.369 L/min, 60° @3.5 bar, SMD=84 um, inner orifice=0.58 mm;

(3) A nozzle that provides a fan-shaped spray, with a flow rate of 0.42 L/min, 60° @3.5 bar, SMD=100 um, inner orifice=1.00 mm.

It should be appreciated that the aforementioned nozzles are just examples and that variances are within the scope of this disclosure.

Figure 15:
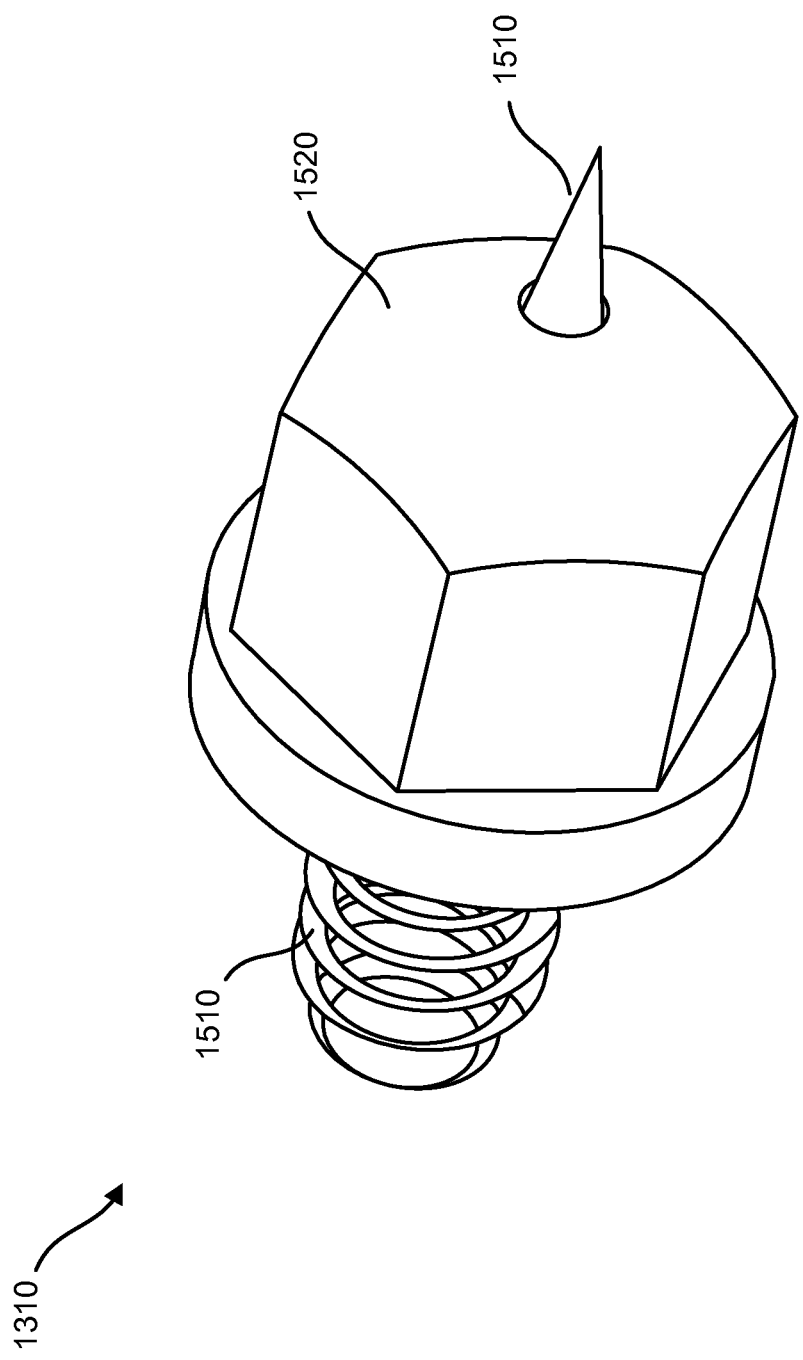
Figure 16:
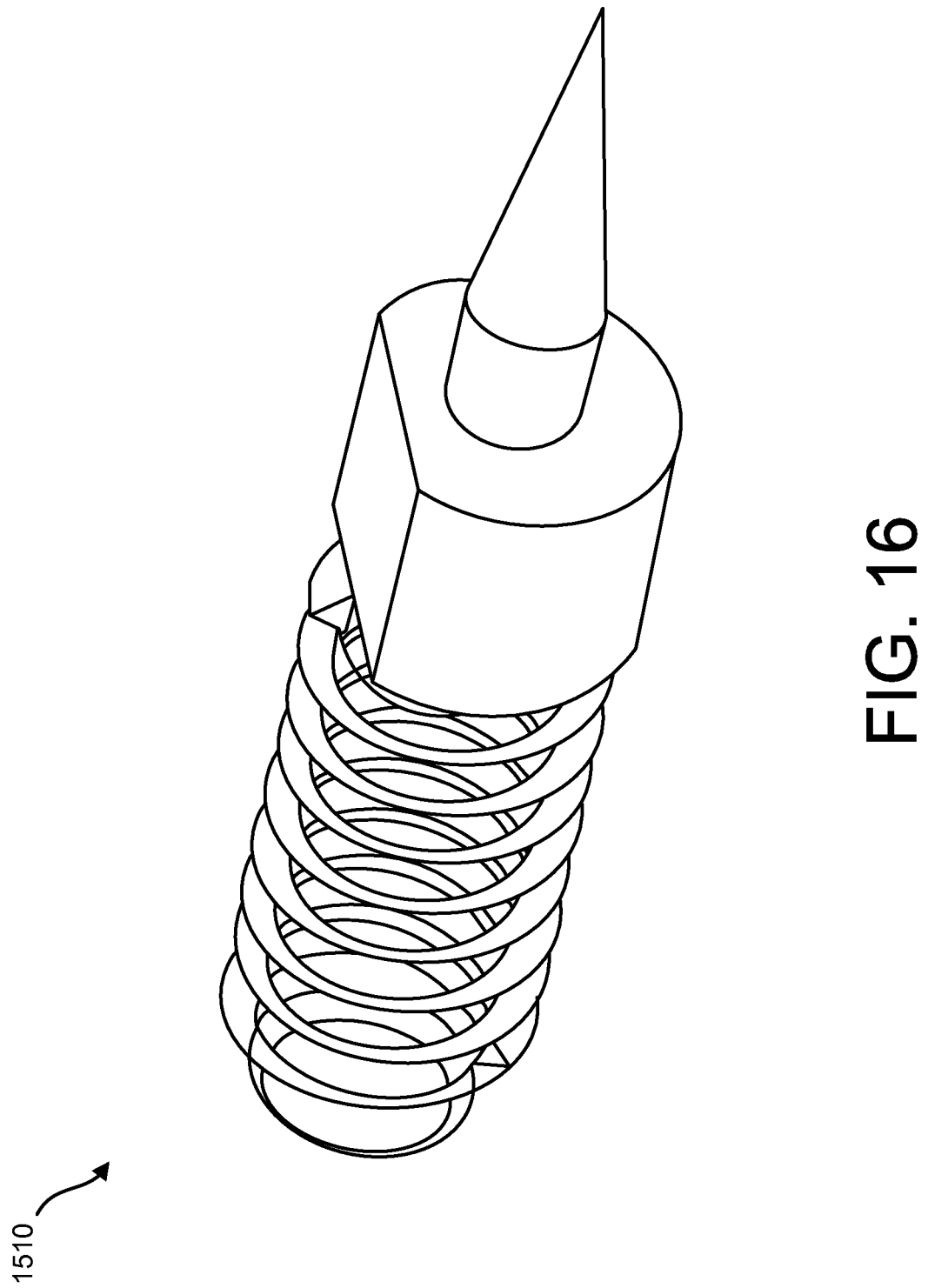
Figure 17:
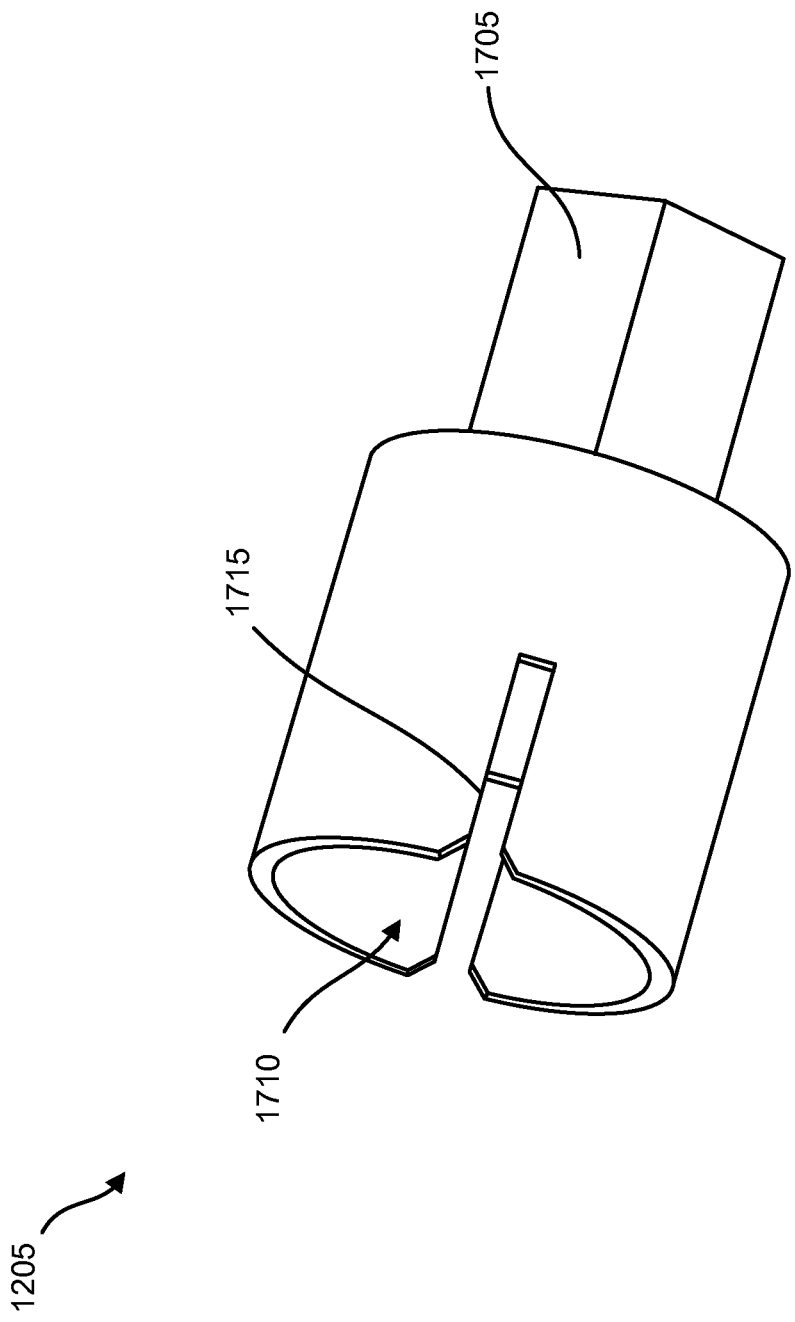

FIG. 15 shows an electrode assembly 1310, which includes a high voltage ion discharge electrode 1510 (or pin) and an insulation element 1520 positioned over the electrode or pin 1510. The insulation element 1520 is sized and shaped so that it covers substantially all of the electrode 1510 and exposes only a front portion of the electrode 1510 in the form of a frontward facing conical tip that is aligned along an axis. FIG. 16 shows the electrode 1510 (sometimes referred to as a pin) without the insulation element 1520. Each high voltage ion discharge electrode in the system has the same structure shown in FIG. 15, a metal pin that is overmolded with plastic at the middle of the pin. Each metal pin has one sharp spike at one end and external screw thread at the other end. The insulation element, which can be plastic, at the middle of pin is for easy gripping during installation and removal, although the pins are not necessarily removable. The plastic is also used to insulate the pin and prevent it from releasing ions from body of pin. The electrode assembly can also be a set of electrode assemblies of the type shown in FIG. 15.

Thus, each electrode assembly 1310 includes an insulator element 1520 that can be formed of a rubber washer that covers a middle section of the electrode, and rubber boot that covers a front section except for a front most, sharpened tip. The rubber washer and a plastic or rubber cap (or boot) isolates the electrode and protects the electrode from static leakage such that only the sharpened tip is exposed and/or uninsulated.

Each high voltage ion discharge electrode is to be screwed into an internal screw thread on the high voltage ring 1120 coupled to the nozzle component 1110. Except for its sharp spike at the end, each high voltage ion discharge electrode is completely covered and concealed by the insulator element after it is installed to the high voltage ring 1120.

Figure 18:
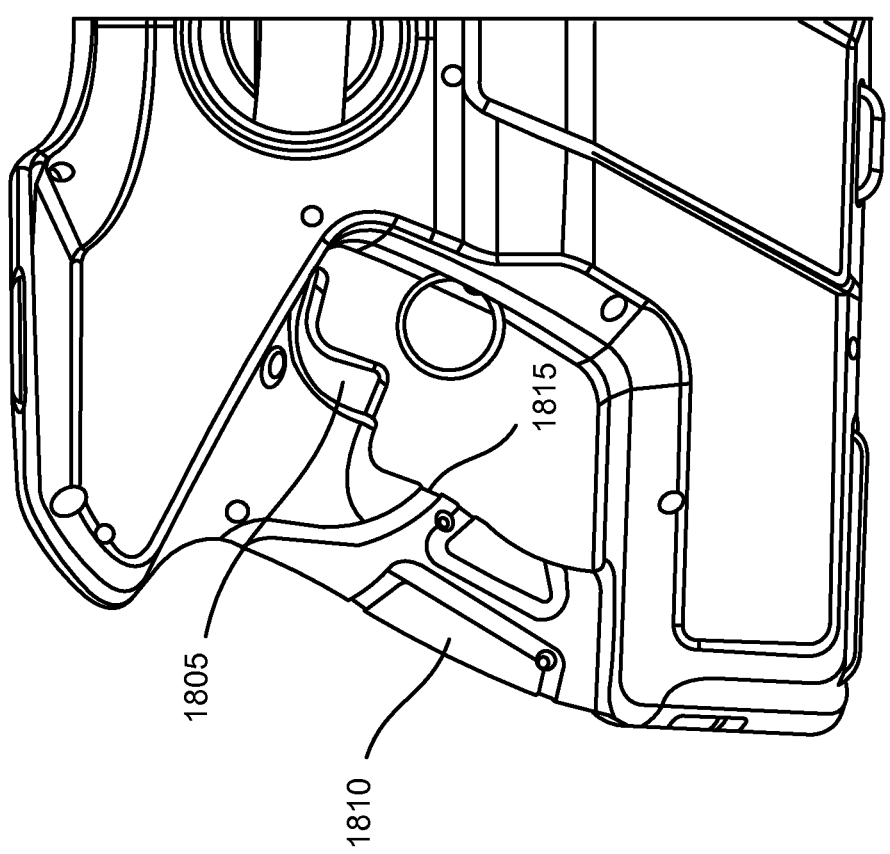

FIG. 18 shows an enlarged view of a handle region of the housing 110. The handle region is ergonomically sized and shaped to be grasped by a single hand of a user. A trigger 1805 or other actuator, such as a knob, switch, etc., is ergonomically positioned so that a user can actuate the trigger with his or her finger when the other fingers are wrapped around a post 1810 of the handle region. A ground wire 1815 or other structure 1815 is embedded into the handle region, such as in the post 1810. The ground wire 1815 is positioned so that it will electrically contact the user's hand when the user grasps the post 1810 during use of the device. In an embodiment, the ground wire is made of copper and is a copper strip of material that contacts the user's hand when the user grasps the device although other materials, such as stainless steel, may be used.

Figure 19:
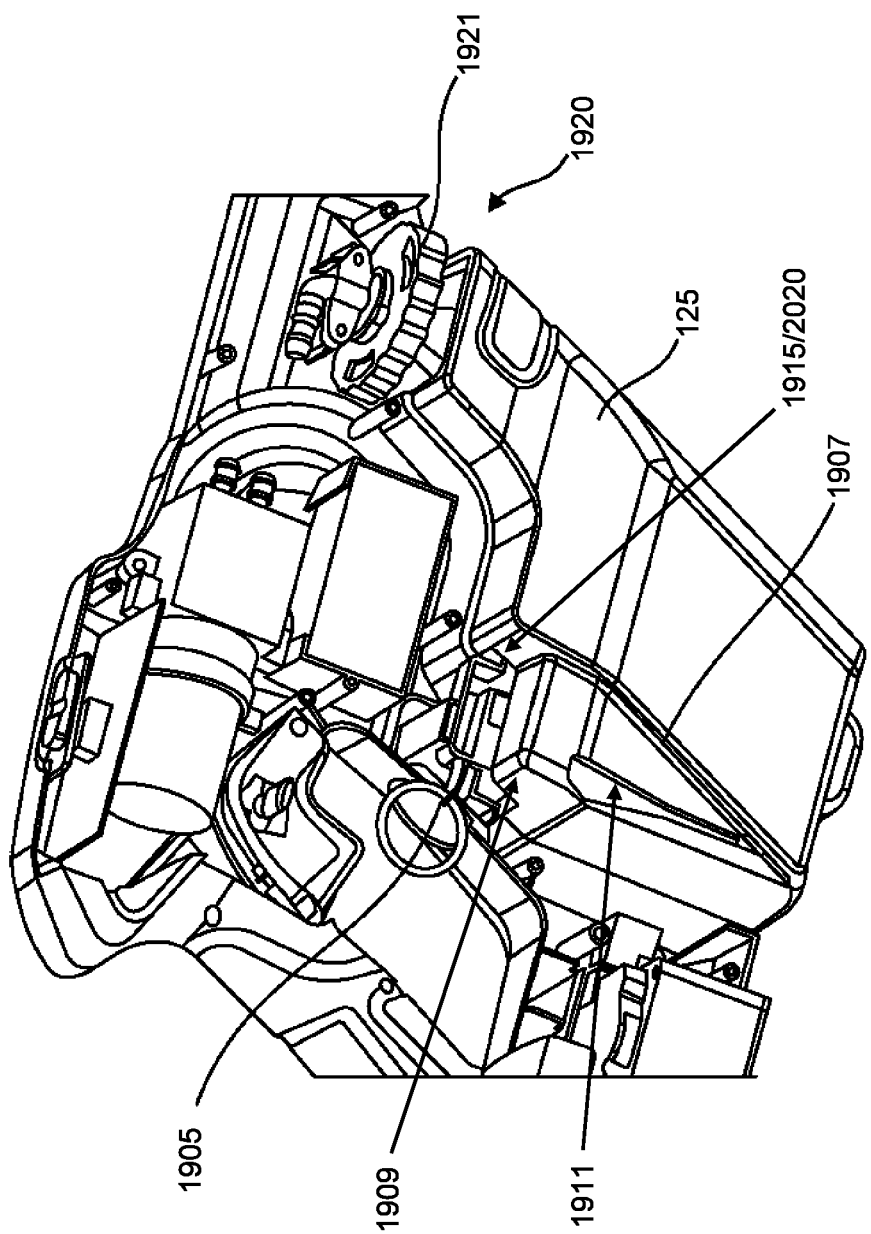

FIG. 19 shows the handle region with a portion of the outer housing 110 removed to show internal components of the device particularly with respect to the reservoir 125, which is a container that encloses an interior cavity that contains fluid. The reservoir is removably attached to the housing 110 and includes a guide surface 1907 that slides into the housing 110. In an embodiment, the guide surface 1907 defines one or more guide projections, such as linear guide projections 1909 and/or inclined guide projections 1911 that interact with the outer housing 110 to properly guide the reservoir 125 into the housing 110.

Figure 20:
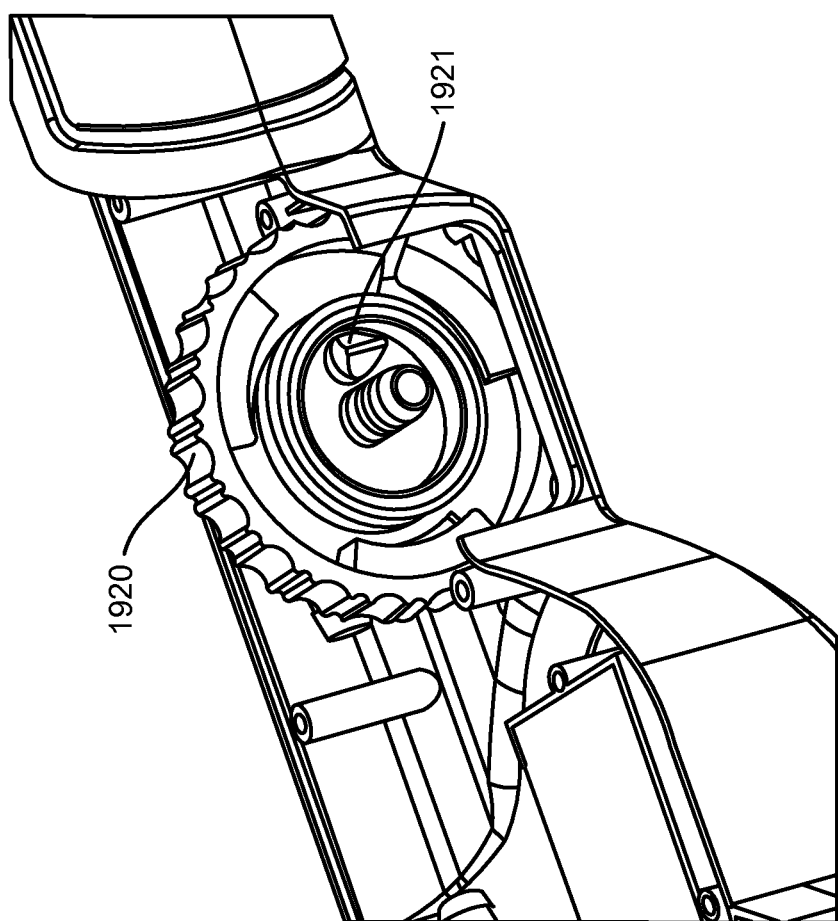

With reference still to FIG. 19, a first detachment mechanism 1905, such as a ring attached to a biased or tensions structure such as a pin, and a second detachment mechanism 1920, such as a rotatable wheel or cap 1921, that can be collectively actuated by a user to enable detachment and locking reattachment of the reservoir 125 to the outer housing. FIG. 20 shows a view of the portion of the cap 1921 that communicates with and covers the interior cavity of the reservoir 125. A one-way valve 2003, such as a duckbill valve, is positioned in the cap 1921 and provides a vent for fluid to enter into the interior of the reservoir from atmosphere as the pump of the system pulls a vacuum in the reservoir.

Figure 21:
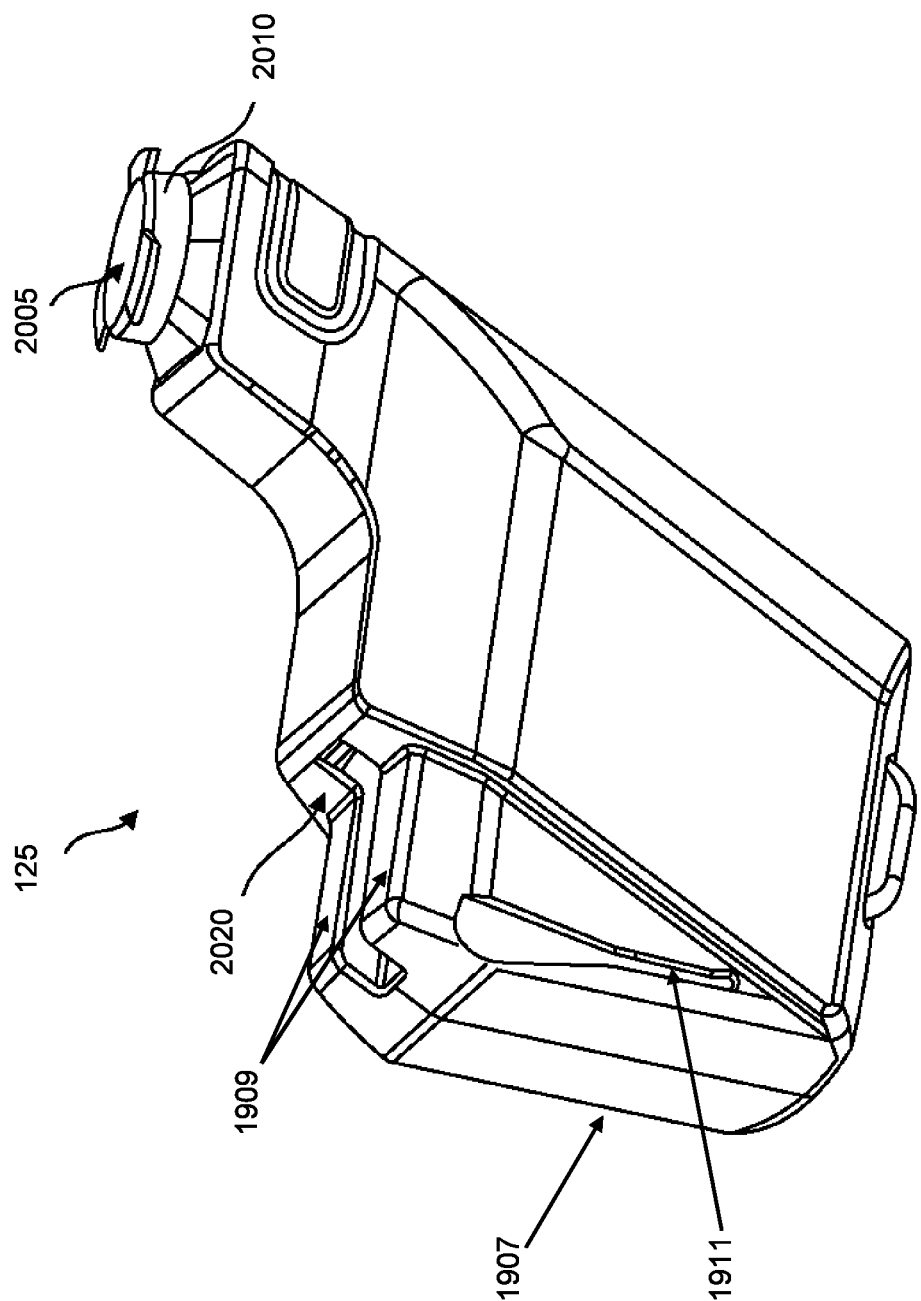

FIG. 21 shows the reservoir 125, which includes an opening 2005 that provides access to the internal cavity of the reservoir 125. The opening 2005 is defined by a neck 2010 having one or more flanges or threads. The neck 2010 sealingly engages the first detachment mechanism 1905 and the second detachment mechanism 1920 of the system for detaching and lockingly attaching the reservoir to the housing.

Figure 22:
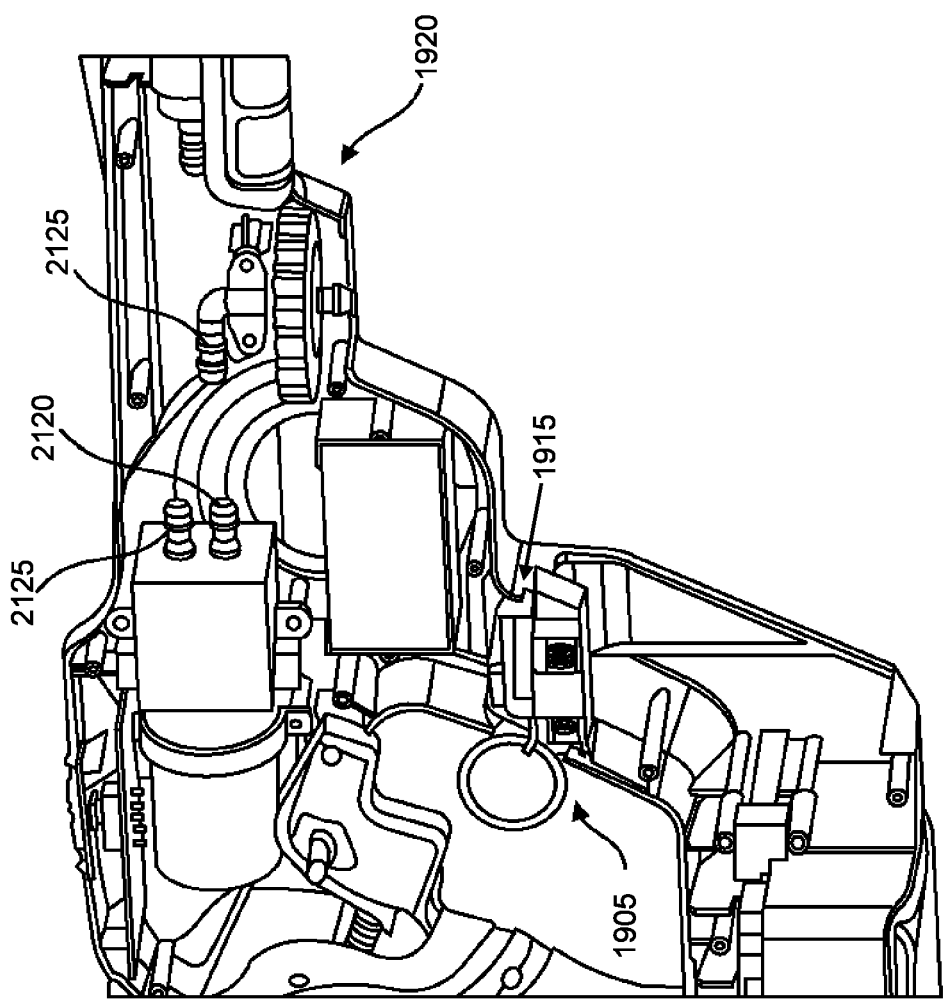

FIG. 22 shows the system with the reservoir 125 and a portion of the outer housing removed. As mentioned, the first detachment mechanism 1905 is configured to attach to the reservoir. Specifically, the first detachment mechanism 1905 includes a spring loaded or tensioned structure having a flange 1915 that is biased toward locking engagement with a seat 2020 (FIG. 21), structure, or opening in the housing of the reservoir. The first detachment mechanism 1905 is biased to automatically engage and lock with the seat 2020 (or other structure) and lock the reservoir 125 to the housing when it is inserted. In this manner, the detachment mechanism 1905 mechanically prevents the reservoir from being removed from the housing unless the user pulls on, disengages, or otherwise releases the first detachment mechanism 1905 from the reservoir. A user can disengage the first detachment mechanism 1905 from the reservoir by pulling on a structure such as a ring or tab of the first detachment mechanism 1905 to release it from the reservoir. Thus the user must pull out the first detachment mechanism relative to the housing and/or reservoir to release the reservoir from the housing.

With reference still to FIG. 22, second detachment mechanism 1920 is a rotatable structure such as a wheel with threads that engage the neck 2010 (FIG. 21) or a portion thereof of the reservoir 125. In an embodiment, the wheel of the second detachment mechanism 1920 is rotated (such as by a three quarter turn or other turn range) by a user once the reservoir 125 is attached to the outer housing. Rotation of a knob the second detachment mechanism 1920 lockingly and sealingly engages the opening 2005 of the reservoir to the knob and to internal conduits of the system that fluidly couple the fluid in the reservoir to the nozzles.

In this regard, an outlet conduit 2115 fluidly communicates with the internal region of the reservoir when the reservoir is attached and lockingly sealed to the housing. The outlet conduit 2115 can be fluidly attached to a pump inlet conduit 2120 of the pump 1005 such as via a hose (not shown). The pump 1005 has an outlet conduit 2125 that can be fluidly attached to the hose coupler 1320 (FIG. 13) of the nozzle assembly. In this manner, the pump can create a pressure differential that draws fluid from the reservoir and drives it to the nozzle assembly.

In an embodiment, a hose or tube connects the outlet conduit 2125 of the pump 1005 to the hose coupler 1320 of the nozzle assembly. The tube (or other conduit) that connects the pump 1005 to the nozzle assembly may be configured to electrostatically charge fluid flowing through the tube by direct charging between the tube, which is charged, and the fluid that flows through the tube toward the nozzles. This is described in more detail with reference to FIG. 24, which shows an ion tube isolator 2405 that electrically charges fluid flowing from the reservoir or pump and toward the nozzles. The ion tube isolator includes the tube 2410 through which fluid passes as well as a high voltage electrode assembly or module 2415 that is electrically connected to the electrostatic module and that is made of a conductive material such as metal. The module 2415 can include a lead where it can be electrically connected to the electrostatic module such as via a conductive wire.

In an embodiment the module 2415 is a conductive material, such as metal. In an embodiment only the module 2415 is conductive and the remainder of the tube 2410 is non-conductive and/or is insulated from contact with any other part of the system. The module 2415 may also be surrounded by an insulator that insulates it from contact with any other part of the system. As fluid flows through the tube 2410, the module 2415 directly contacts the fluid as it flows and passes a charge to the fluid through direct contact with the fluid. In this way, the ion tube isolator 2405 electrostatically charges the fluid prior to the fluid passing through the nozzle.

Figure 23:
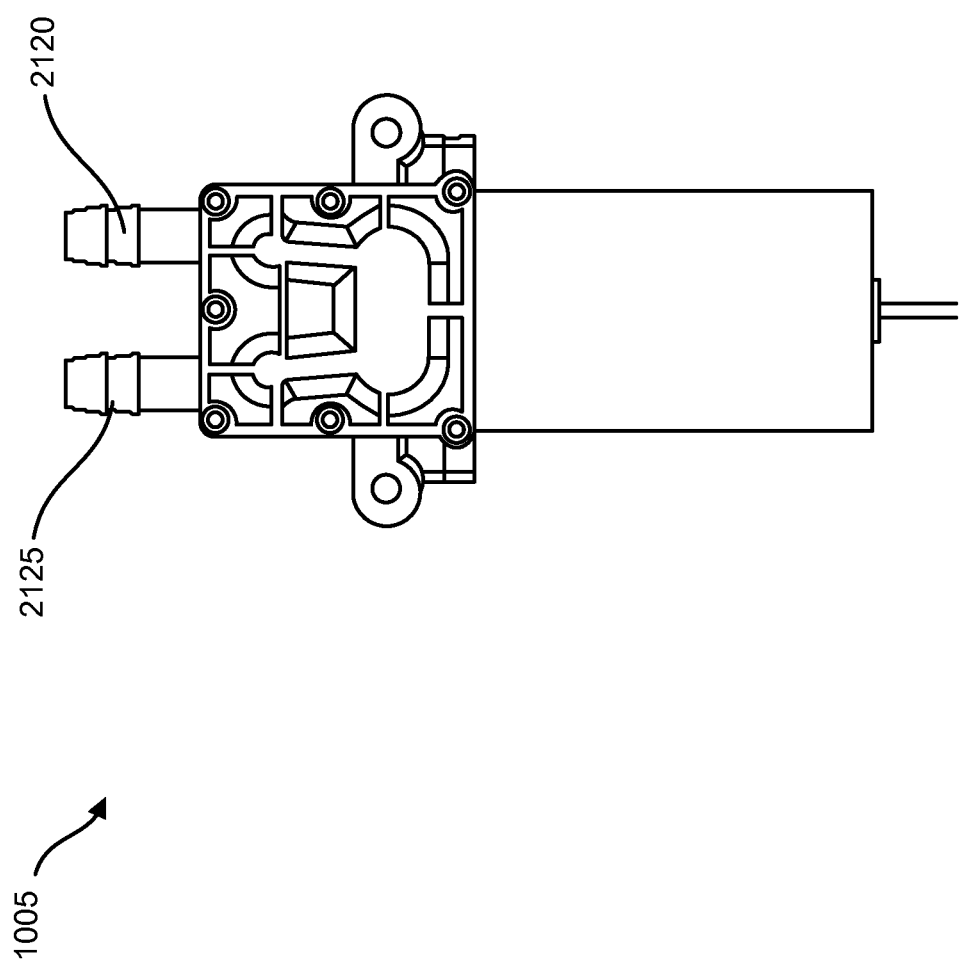

In an embodiment, the pump 1005 is a direct current (DC) pump. The pump includes a rotary motion motor with a connecting rod that drives a diaphragm in an up and down motion when activated. In the process of the downward movement of the diaphragm, a pump cavity creates a pressure differential such as by pulling a vacuum relative to the interior of the reservoir to suck fluid through the pump inlet conduit 2120 from the reservoir. Upward movement of the diaphragm pushes fluid of the pump cavity press through the pump outlet conduit 2125 toward the hose coupler 1320 of the nozzle assembly via an attachment hose that attaches the pump outlet conduit 2125 to the hose coupler 1320. Any mechanical transmission parts and the pump cavity are isolated by the diaphragm within the pump. The diaphragm pump does not need oil for auxiliary lubricating, in the process of transmission, extraction and compression of the fluid. FIG. 23 shows an exemplary embodiment of the pump 1005, which includes the pump inlet conduit 2120 and the pump outlet conduit 2125.

In use, the user grasps the system 105 and powers the pump so that it propels fluid out of the selected nozzle from the reservoir. As mentioned, the user can use the nozzle tool 1205 to both insert and lock the nozzle assembly 1015 to the system. The user can also use the nozzle tool 1205 to rotate the nozzle component and fluidly couple a selected nozzle to the reservoir. Thus the user can select a desired plume profile for the fluid. The system can also be equipped with just a single nozzle. The user also activates the electrostatic module so that the electrodes become charged and form an electrostatic field in the electrode ring. The fluid is propelled from the nozzle through the ring and through the electrostatic field so that the droplets of fluid in the aerosol plume become positively or negatively electrically charged. As mentioned, the electrodes and the nozzle are aligned along a common parallel axis. This directs the liquid or aerosol toward a desired object based on where the user points the nozzles. In an embodiment, the electrodes do not physically contact the fluid propelled through the nozzles. In another embodiment, the electrodes physically contact the fluid propelled through the nozzles While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results.

The invention claimed is:

1. An electrostatic sprayer apparatus comprising:
    a main body housing configured to receive a power source;
    a nozzle assembly disposed at a first end of the main body housing;
    a reservoir configured to have a fluid disposed (herein, wherein the reservoir is releasably attachable to the main body housing and is configured for fluid communication with the nozzle assembly when attached to the main body housing, the reservoir comprising:
        a reservoir housing comprising a first linear guide projection and a second linear guide projection, the first linear guide projection and the second linear guide projection disposed in a parallel orientation on a guide surface of the reservoir housing and configured for alignment of the reservoir housing with the main body housing for attachment thereto, the first linear guide projection configured to interact with a first corresponding surface of the main body housing and the second linear guide projection configured to interact with a second corresponding surface of the main body housing;
        an internal cavity defined by an interior surface of the reservoir housing and configured to receive the fluid;
        an opening in the reservoir housing, the opening configured to enable the receiving of the fluid into the internal cavity; and
        a neck defining the opening in the reservoir housing, the neck projecting outwardly from the reservoir housing, wherein each of the first linear guide projection and the second linear guide projection on the guide surface of the reservoir housing is discrete of the neck;
    one or more detachment mechanisms, the one or more detachment mechanisms configured for lockingly attaching the reservoir to the main body housing and releasing the reservoir from the main body housing, wherein at least one of the one or more detachment mechanisms comprises a flange on the main body housing, a complementary structure of the reservoir configured for locking engagement with the flange, and a release structure, the release structure comprising one of a tab or a ring configured to be gripped and pulled by a user for unlocking disengagement of the flange from the complementary structure of the reservoir;
    a pump disposed within the main body housing, the pump configured to be powered by the power source and to pump at least a portion of the fluid from the reservoir to the nozzle assembly for dispensing the electrostatically charged at least portion of the fluid through the nozzle assembly to an exterior of the electrostatic sprayer apparatus;
    an electrostatic module disposed within the main body housing;
    at least one electrode assembly in electrical communication with the electrostatic module via a conductive wire, the at least one electrode assembly configured for electrostatic charging of the at least portion of the fluid; and
    a cap assembly configured to mate with the neck of the reservoir to occlude the opening, the cap assembly further configured to, when the reservoir is attached to the main body housing, form a seal between the reservoir and the pump and enable the fluid communication between the reservoir and the nozzle assembly.

2. The electrostatic sprayer apparatus of claim 1, wherein the first linear guide projection is configured for insertion into the main body housing along the first corresponding surface and the second linear guide projection is configured for insertion into the main body housing along the second corresponding surface.

3. The electrostatic sprayer apparatus of claim 1, wherein the neck comprises at least one of one or more flanges or one or more threads, the one or more flanges or the one or more threads configured to sealingly engage with an interior surface of the cap assembly.

4. The electrostatic sprayer apparatus of claim 1, wherein the reservoir and the cap assembly are configured such that, when the reservoir is attached to the main body housing, the cap assembly mated with the neck of the reservoir is disposed inside of the main body housing.

5. The electrostatic sprayer apparatus of claim 1, wherein the opening is disposed in a top surface of the reservoir housing.

6. The electrostatic sprayer apparatus of claim 1, further comprising a one-way valve in fluid communication with the reservoir, the one-way valve configured to vent atmospheric fluid into the internal cavity as the pump generates a vacuum in the reservoir.

7. The electrostatic sprayer apparatus of claim 6, wherein the one-way valve comprises a duckbill valve.

8. The electrostatic sprayer apparatus of claim 1, wherein the cap assembly comprises a cap body and a conduit disposed through the cap body, the cap body configured to sealingly engage with the neck of the reservoir, the conduit configured for fluid communication with the pump.

9. The electrostatic sprayer apparatus of claim 1, further comprising a grounded ring disposed at the first end of the main body housing, the grounded ring being distal relative to the nozzle assembly.

10. The electrostatic sprayer apparatus of claim 1, further comprising the power source, wherein the power source comprises a lithium ion battery.

11. The electrostatic sprayer apparatus of claim 1, further comprising:
    a handle attached to the main body housing; and a first actuator disposed in the handle, the first actuator configured to enable a user to activate the pump.

12. The electrostatic sprayer apparatus of claim 11, further comprising a second actuator, the second actuator configured to enable the user to activate the electrostatic module.

13. The electrostatic sprayer apparatus of claim 1, wherein the at least one electrode assembly comprises a first electrode assembly disposed in a flow pathway between the pump and the nozzle assembly, the first electrode assembly configured for direct charging of the at least portion of the fluid as it passes through the flow pathway.

14. The electrostatic sprayer apparatus of claim 13, wherein the first electrode assembly comprises a conductive tube disposed within an insulator, the insulator and the conductive tube defining a first portion of the flow pathway, the insulator and the conductive tube in fluid communication with an outlet of the pump and an inlet of the nozzle assembly, and wherein at least one of an outlet of the pump or an inlet of the nozzle assembly is in fluid communication with the insulator and the conductive tube via one or more hoses, the one or more hoses defining a remainder of the flow pathway.

15. The electrostatic sprayer apparatus of claim 13, wherein the at least one electrode assembly further comprises a second electrode assembly disposed in the nozzle assembly, the second electrode assembly configured for indirect electrostatic charging of the at least portion of the fluid as it passes through the nozzle assembly to the exterior of the electrostatic sprayer apparatus.

16. The electrostatic sprayer apparatus of claim 1, wherein the nozzle assembly comprises a rotatable component and two or more nozzles coupled to the rotatable component, the nozzle assembly configured to, via rotation of the rotatable component and alignment of one of the two more nozzles with an outlet of the nozzle assembly, enable selection of a specified plume profile for the electrostatically charged portion of the fluid during the dispensing thereof through the nozzle assembly to the exterior of the electrostatic sprayer apparatus.

17. An electrostatic sprayer apparatus comprising:
a main body housing configured to receive a power source;
a nozzle assembly disposed at a first end of the main body housing;
a reservoir configured to have a fluid disposed therein, wherein the reservoir is releasably attachable to the main body housing and is configured for fluid communication with the nozzle assembly when attached to the main body housing, the reservoir comprising:
a reservoir housing comprising a first linear guide projection and a second linear guide projection, the first linear guide projection and the second linear guide projection disposed in a parallel orientation on a guide surface of the reservoir housing and configured for alignment of the reservoir housing with the main body housing f r attachment thereto, the first linear guide projection configured to interact with a first corresponding surface of the main body housing and the second linear guide projection configured to interact with a second corresponding surface of the main body housing;
an internal cavity defined by an interior surface of the reservoir housing and configured to receive the fluid; and
an opening disposed in a top surface of the reservoir housing, the opening configured to enable the receiving of the fluid into the internal cavity, the opening defined by a neck having at least one of one or more flanges or one or more threads;
one or more detachment mechanisms, the one or more detachment mechanisms configured for lockingly attaching the reservoir to the main body housing and releasing the reservoir from the main body housing, wherein at least one of the one or more detachment mechanisms comprises a flange on the main body housing, a complementary structure of the reservoir that is configured for locking engagement with the flange, and a release structure, the release structure comprising one of a tab or a ring configured to be gripped and pulled by a user for unlocking disengagement of the flange from the complementary structure of the reservoir;
a pump disposed within the main body housing, the pump configured to be powered by the power source and to pump at least a portion of the fluid from the reservoir to the nozzle assembly for dispensing the at least portion of the fluid through the nozzle assembly to an exterior of the electrostatic sprayer apparatus;
a one-way valve in fluid communication with the reservoir, the one-way valve configured to vent atmospheric fluid into the internal cavity as the pump generates a vacuum in the reservoir;
an electrostatic module disposed within the main body housing;
at least one electrode assembly in electrical communication with the electrostatic module via a conductive wire, the at least one electrode assembly configured for electrostatic charging of the at least portion of the fluid; and
a cap assembly configured to mate with the neck of the reservoir to occlude the opening, the cap assembly comprising:
a cap body configured to threadedly engage with the one or more flanges or the one or more threads of the neck for the mating thereto; and
a conduit disposed through the cap body, the conduit configured for fluid communication with the pump;
wherein the cap assembly is further configured to, when the reservoir is attached to the main body housing, form a seal between the reservoir and the pump and enable the fluid communication between the reservoir and the nozzle assembly; and
wherein the reservoir and the cap assembly are configured such that, when the reservoir is attached to the main body housing, the cap assembly mated with the neck of the reservoir is disposed inside of the main body housing.

18. The electrostatic sprayer apparatus of claim 17, wherein the first linear guide projection is configured for insertion into the main body housing along the first corresponding surface and the second linear guide projection is configured for insertion into the main body housing along the second corresponding surface.

19. The electrostatic sprayer apparatus of claim 17, wherein the one-way valve comprises a duckbill valve.

20. The electrostatic sprayer apparatus of claim 17, further comprising:
a handle attached to the main body housing; and
a first actuator disposed in the handle, the first actuator configured to enable a user to activate the pump.

21. The electrostatic sprayer apparatus of claim 20, further comprising a second actuator, the second actuator configured to enable the user to activate the electrostatic module.

22. The electrostatic sprayer apparatus of claim 17, wherein the at least one electrode assembly comprises a first electrode assembly disposed in a flow pathway between the pump and the nozzle assembly, the first electrode assembly configured for direct charging of the at least portion of the fluid as it passes through the flow pathway, wherein the first electrode assembly comprises a conductive tube disposed within an insulator, the insulator and the conductive tube defining a first portion of the flow pathway, the insulator and the conductive tube in fluid communication with the pump and the nozzle assembly, and wherein at least one of an outlet of the pump or an inlet of the nozzle assembly is in fluid communication with the insulator and the conductive tube via one or more hoses, the one or more hoses defining a remainder of the flow pathway.

23. The electrostatic sprayer apparatus of claim 22, wherein the at least one electrode assembly further comprises a second electrode assembly disposed in the nozzle assembly, the second electrode assembly configured for indirect electrostatic charging of the at least portion of the fluid as it passes through the nozzle assembly to the exterior of the electrostatic sprayer apparatus.

24. The electrostatic sprayer apparatus of claim 17, wherein the nozzle assembly comprises a rotatable component and two or more nozzles coupled to the rotatable component, the nozzle assembly configured to, via rotation of the rotatable component and alignment of one of the two more nozzles with an outlet of the nozzle assembly, enable selection of a specified plume profile for the electrostatically charged at-least-portion of the fluid during the dispensing thereof through the nozzle assembly to the exterior

UNITED STATES PATENT AND TRADEMARK OFFICE
CERTIFICATE OF CORRECTION

PATENT NO. : 10,994,291 B2
APPLICATION NO. : 17/090820
DATED : May 4, 2021
INVENTOR(S) : Clifford Wright Page 1 of 1

It is certified that error appears in the above-identified patent and that said Letters Patent is hereby corrected as shown below:

In the Claims

Column 11; Claim 1, Line 32 change "(herein" to "therein"

Column 13; Claim 17, Line 56 change "f r" to "for"

Column 15; Claim 24, Line 30 change "at-least-portion" to "portion"

Signed and Sealed this
Fifteenth Day of June, 2021

Drew Hirshfeld
*Performing the Functions and Duties of the*
*Under Secretary of Commerce for Intellectual Property and*
*Director of the United States Patent and Trademark Office*